United States Patent
Jacobson et al.

(10) Patent No.: US 8,425,469 B2
(45) Date of Patent: *Apr. 23, 2013

(54) SYSTEMS AND METHODS FOR CONTROLLED SUBSTANCE DELIVERY NETWORK

(75) Inventors: Andrew D. Jacobson, San Antonio, TX (US); Jeff Sommers, San Antonio, TX (US); Rasmus T. Kölln, Kiel (DE); Kenneth R. Rose, San Antonio, TX (US)

(73) Assignee: Jacobson Technologies, LLC, San Antonio, TX (US)

( * ) Notice: Subject to any disclaimer, the term of this patent is extended or adjusted under 35 U.S.C. 154(b) by 1024 days.

This patent is subject to a terminal disclaimer.

(21) Appl. No.: 12/107,470

(22) Filed: Apr. 22, 2008

(65) Prior Publication Data
US 2008/0306437 A1   Dec. 11, 2008

Related U.S. Application Data

(60) Provisional application No. 60/925,881, filed on Apr. 23, 2007.

(51) Int. Cl.
  *A61M 5/00*   (2006.01)
  *A01K 29/00*   (2006.01)
(52) U.S. Cl.
  USPC .......................................... 604/246; 119/174
(58) Field of Classification Search .......... 604/131–157, 604/67, 19, 246; 119/174, 158, 159, 656; 4/597, 604; 600/365; 370/351; 128/200.11
See application file for complete search history.

(56) References Cited

U.S. PATENT DOCUMENTS

| 4,464,178 A | 8/1984 | Dalton |
| 4,687,468 A | 8/1987 | Gianturco |

(Continued)

FOREIGN PATENT DOCUMENTS

| WO | 9956117 | 11/1999 |
| WO | 0236044 | 10/2002 |
| WO | 2005079891 | 1/2005 |
| WO | 2010144533 | 12/2010 |

OTHER PUBLICATIONS

"PHM-111-EC Advanced Syringe Pump with Computer Control" http://www.med-associates.com/pumps/phm111.htm#111ec, web page update date: Aug. 15, 2008 (4 pages).

(Continued)

*Primary Examiner* — Nicholas Lucchesi
*Assistant Examiner* — Pritesh Patel
(74) *Attorney, Agent, or Firm* — Meyertons, Hood, Kivlin, Kowert & Goetzel, P.C.; Eric B. Meyertons

(57) ABSTRACT

In various embodiments, multiple pumps may be used to deliver substances to multiple respective animals. A computer system may send/receive information to/from the pumps (e.g., to control and monitor various aspects of the pumps and/or store information associated with the pump). In some embodiments, the computer system may determine respective controlled delivery rates for the pumps (e.g., based in part on a weight of an animal receiving the substance from the respective pump) and send the determined controlled delivery rates to the respective pumps. The computer system may also receive user identifications from operators controlling a pump (e.g., in response to a pump alarm) and documentation indicators entered by the operator and/or pump to use in documenting pump activity.

24 Claims, 25 Drawing Sheets

U.S. PATENT DOCUMENTS

| | | | |
|---|---|---|---|
| 4,781,695 A | | 11/1988 | Dalton |
| 4,784,646 A | | 11/1988 | Feingold |
| 4,857,053 A | | 8/1989 | Dalton |
| 4,861,341 A | | 8/1989 | Woodburn |
| 4,889,528 A | | 12/1989 | Nadai et al. |
| 5,104,374 A | | 4/1992 | Bishko et al. |
| 5,328,465 A | | 7/1994 | Kratoska et al. |
| 5,560,317 A | * | 10/1996 | Bunyan et al. ............... 119/174 |
| 5,637,088 A | | 6/1997 | Wenner et al. |
| 5,792,056 A | | 8/1998 | Prince |
| 5,813,972 A | | 9/1998 | Nazarian et al. |
| 5,989,239 A | | 11/1999 | Finch et al. |
| 6,007,516 A | | 12/1999 | Burbank et al. |
| 6,039,712 A | | 3/2000 | Fogarty et al. |
| 6,293,922 B1 | | 9/2001 | Haase |
| 6,542,850 B2 | | 4/2003 | Ulman et al. |
| 6,544,214 B1 | | 4/2003 | Utterberg |
| 6,558,347 B1 | | 5/2003 | Jhuboo et al. |
| 6,595,756 B2 | | 7/2003 | Gray et al. |
| 6,616,630 B1 | | 9/2003 | Woehr et al. |
| 6,685,668 B1 | | 2/2004 | Cho et al. |
| 6,690,280 B2 | | 2/2004 | Citrenbaum et al. |
| 6,740,072 B2 | | 5/2004 | Starkweather et al. |
| 6,790,198 B1 | | 9/2004 | White et al. |
| 6,864,914 B1 | | 3/2005 | Birk |
| 6,940,403 B2 | | 9/2005 | Kail, IV |
| 6,998,980 B2 | | 2/2006 | Ingley, III et al. |
| 7,050,887 B2 | | 5/2006 | Alvarez |
| 7,056,307 B2 | | 6/2006 | Smith et al. |
| 7,056,316 B1 | | 6/2006 | Burbank et al. |
| 7,059,275 B2 | | 6/2006 | Laitinen et al. |
| 7,204,823 B2 | | 4/2007 | Estes et al. |
| 7,236,936 B2 | | 6/2007 | White et al. |
| 7,269,516 B2 | | 9/2007 | Brunner et al. |
| 7,300,418 B2 | | 11/2007 | Zaleski |
| 7,347,819 B2 | | 3/2008 | Lebel et al. |
| 7,347,854 B2 | | 3/2008 | Shelton et al. |
| 7,628,776 B2 | | 12/2009 | Gibson et al. |
| 2003/0050621 A1 | | 3/2003 | Lebel et al. |
| 2003/0050626 A1 | | 3/2003 | Gibson et al. |
| 2004/0171983 A1 | | 9/2004 | Sparks |
| 2004/0181314 A1 | | 9/2004 | Zaleski |
| 2005/0102167 A1 | | 5/2005 | Kapoor |
| 2005/0215982 A1 | | 9/2005 | Malave et al. |
| 2006/0053036 A1 | | 3/2006 | Coffman et al. |
| 2006/0058774 A1 | | 3/2006 | Delnevo et al. |
| 2007/0114294 A1 | | 5/2007 | Ashton, Jr. |
| 2007/0128047 A1 | | 6/2007 | Gonnella et al. |
| 2007/0251835 A1 | | 11/2007 | Mehta et al. |
| 2007/0253021 A1 | | 11/2007 | Mehta et al. |
| 2007/0253380 A1 | | 11/2007 | Jollota et al. |
| 2007/0254593 A1 | | 11/2007 | Jollota et al. |
| 2007/0255116 A1 | | 11/2007 | Mehta et al. |
| 2007/0255125 A1 | | 11/2007 | Moberg et al. |
| 2007/0255126 A1 | * | 11/2007 | Moberg et al. ............... 600/365 |
| 2007/0255250 A1 | | 11/2007 | Moberg et al. |
| 2007/0255348 A1 | | 11/2007 | Holtzclaw |
| 2007/0258395 A1 | | 11/2007 | Jollota et al. |
| 2008/0033360 A1 | | 2/2008 | Evans et al. |
| 2008/0306437 A1 | | 12/2008 | Jacobson et al. |
| 2009/0053086 A1 | | 2/2009 | Navarro |
| 2009/0196775 A1 | | 8/2009 | Navarro |
| 2009/0234275 A1 | * | 9/2009 | Jacobson et al. ............... 604/31 |
| 2009/0234285 A1 | * | 9/2009 | Jacobson et al. ............... 604/111 |
| 2009/0234286 A1 | * | 9/2009 | Jacobson et al. ............... 604/111 |
| 2011/0087189 A1 | | 4/2011 | Jacobson et al. |

OTHER PUBLICATIONS

"NE 1000 Family Detailed Features" web archive address: http://web.archive.org/web/20060209012340/http://www.syringepump.com/detailedfeatures.htm; web archive dated Feb. 9, 2006 (4 pages).

Co-pending U.S. Appl. No. 12/107,470 entitled "Systems and Methods for Controlled Substance Delivery Network", to Jacobson et al., filed Apr. 22, 2008.

Co-pending U.S. Appl. No. 12/426,090 entitled "Controlled Substance Distribution Network Systems and Methods Thereof", to Jacobson et al., filed Apr. 17, 2009.

Co-pending U.S. Appl. No. 12/426,102 entitled "Systems and Methods for Controlled Substance Distribution Network", to Jacobson et al., filed Apr. 17, 2009.

Co-pending U.S. Appl. No. 12/426,086 entitled "Controlled Substance Distribution Network Systems and Methods Thereof", to Jacobson et al., filed Apr. 17, 2009.

Co-pending U.S. Appl. No. 12/796,874 entitled "Controlled Delivery of Substances System and Method", to Jacobson et al., filed Jun. 9, 2010.

Co-pending U.S. Appl. No. 11/836,738 entitled "Improved Medical Device with Septum", to Jacobson et al., filed Aug. 9, 2007.

"Instech Solomon" Apr. 2007. (pp. 1-57).

International Search Report and Written Opinion for PCT/US2010/037905, mailed Aug. 20, 2010. (pp. 1-15).

USPTO Office Communication for U.S. Appl. No. 12/426,090 mailed Jan. 7, 2011.

USPTO Office Communication for U.S. Appl. No. 12/426,102 mailed Jan. 7, 2011.

USPTO Office Communication for U.S. Appl. No. 11/836,738 mailed Oct. 13, 2010.

USPTO Office Communication for U.S. Appl. No. 11/836,738 mailed Apr. 18, 2011.

USPTO Office Communication for U.S. Appl. No. 11/836,738 mailed Jun. 15, 2011.

* cited by examiner

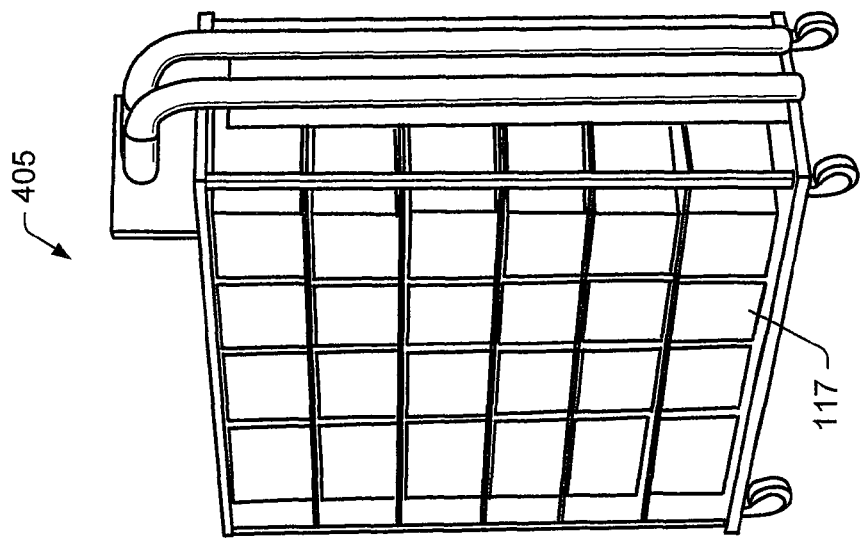
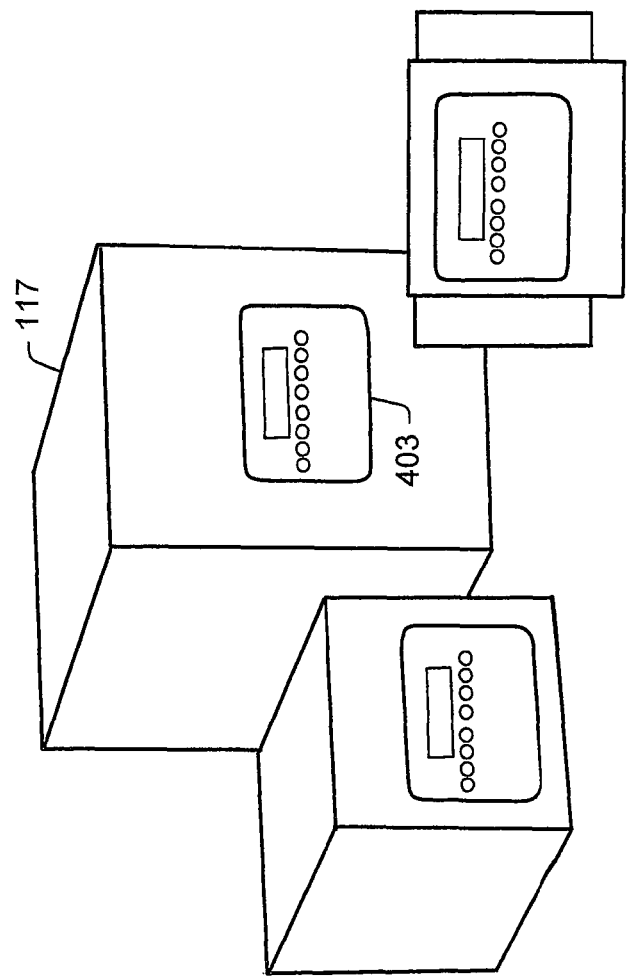
FIG. 5

Wizard

→ General Information
*Here you can enter general information about the study. This data later helps you to identify the need of this study*

◇ Security
◇ Pump Configuration
◇ Alert Settings
◇ Infusion Program

The Wizard helps you with the initial Set up of a project. It enables you to Match pumps against animals for an easier identification through out the study and it enables you to group the animals.
If you have any problems with this wizard, please refer to the manual chapter wizard which gives you further information.

You are able to do all the settings of this wizard without the wizard. It is only recommended to use the wizard for the initial set up.

Please insert the data of the company in this screen for Whom the study is for. This will help you to identify the need of the study later on.

The start date of the study is most likely the date today. Please insert the date when the study is likely to start. This will not be the date when the pumps are running according to the pump profile, it is just a date for documentation purposes.

The study director should be the person who is setting up the study, also known as the Administrator. He has all the rights to add and delete controllers and monitors of the study and he is able to stop and start a study. Most likely this will be your name.

Study Name: _____
Company Name: _____
Department: _____

Study start date: 25. February 2008 ⌄

Study director: _____
Study technician: _____

Step 1 of 5:

[< Previous] [Next >] [Skip >>] [Cancel]

| Wizard | _ □ × |

◈ General Information
↑ Security
　Here you get assistance in
　Setting up the security
　information of the project.
　Security settings are
　handled with care, so please
　take your time and complete
　this part carefully.
◇ Pump Configuration
◇ Alert Settings
◇ Infusion Program

The wizard will help you to set up
The security settings according to
your needs.
If you have any problems with this
wizard, please refer to the manual
chapter wizard subsection security
settings.

Security settings are an important
feature. Your software supports 3
kinds of security permission, the
Administrator who is allowed to do
everything,
The Controller who is the technician
of the study and is able to modify
pump settings
And the Monitor, who is only allowed
to see information of the project but is
not allowed to do changes.

Please choose how detailed you want the security settings
to be. Be aware that there might be security policies in your
firm, you might confirm with.

After your selection, please put in the Data for the users. If
you want to add more users then which are available here,
please go to the user config menu after you have finished
the wizard setup and add the missing users.
You are able to add and delete users always with the user
config menu.

It might be much more comfortable to export user data of an
old study and do an import in this study. Please refer to your
manual on how to do that.

⦿ One person only
○ Administrator and Controllers
○ Detailed security setup

Administrator Password: [            ]

Step 2 of 5:
▬

[ < Previous ]　[ Next > ]　[ Skip >> ]　[ Cancel ]

FIG. 12

To be loaded at 2:00 pm Thursday December 3

| Future Dose | Syringe ID |
|---|---|
| 20 ml | #356 |
| 30 ml | #245 |
| 23 ml | #785 |
| 10 ml | #754 |
| 14 ml | #748 |
| 34 ml | #934 |

SYSTEMS AND METHODS FOR CONTROLLED SUBSTANCE DELIVERY NETWORK

PRIORITY CLAIM

This application claims the benefit of priority of U.S. Provisional Patent Application Ser. No. 60/925,881 titled "Information network including medical infusion pumps and other medical devices", filed on Apr. 23, 2007, whose inventors are Andrew D. Jacobson and Jeff Sommers, which is hereby incorporated by reference in its entirety as though fully and completely set forth herein.

BACKGROUND

The pharmaceutical industry, contract research organizations, academia, and government entities routinely test the efficacy and safety of new chemical entities using intravenous (usually) infusion in lab animals including, for example, rats, dogs and nonhuman primates. While some acute infusion studies may be performed in a small number of lab animals (e.g., $\leqq 10$) over several minutes or hours, large-scale "toxicology" infusion studies of, for example, several hundred rats or, for example, 10's of larger animals such as dogs or nonhuman primates for periods lasting, for example, from 30-90 days may also be performed.

Medical infusion pumps (e.g., electromechanical medical infusion pumps) may be used during these studies (as well as in other veterinary and/or human medical applications). There are numerous types of electromechanical medical infusion pumps including syringe, peristaltic, diaphragm, large volume, stationary ("pole mount"), and portable ("ambulatory"). These pumps may be used to deliver a substance (such as a drug) at a controlled delivery rate to, for example, a laboratory test animal. Lab animal infusion and human-use infusion may share similar pump technology. The methods of use in each field may differ in that human-use infusion (e.g., in a healthcare application) may be tailored to a single patient's needs while lab animal infusion (e.g., in an industrial application) may apply common parameters to multiple animals.

Animals may be connected to a medical infusion pump (for example, a syringe pump, though other pumping mechanisms may also be used) through a catheter, tubing, tether, fluid swivel, etc. Usually, one pump is used per animal and operators may program and monitor each pump manually. Operators may manually enter a delivery rate into a pump, load a substance-filled syringe for the pump, and then activate the pump (e.g., by pressing a start button). Operators may also interact with numerous medical and monitoring devices involved in the study. The process of loading, starting, and stopping the pump, recording data from medical and monitoring devices, and, for example, responding to pump alarms may be manually documented by the operator (e.g., on a clipboard). Because studies often involve large numbers of animals, manually setting up numerous pumps may be time consuming and tedious. In addition, Good Laboratory Practices (GLP's) (including documentation of processes, data collection, and study results) are required by regulatory agencies such as the Food and Drug Administration (FDA). Manually documenting the processes, data collection, and study results may also be time consuming, tedious and subject to human error.

SUMMARY

In various embodiments, a pump may receive a controlled delivery rate (e.g., from a computer system) to be used to deliver a substance to an animal (e.g., to study the effects of the substance on the respective animal). In some embodiments, multiple pumps may communicate with the computer system and may be used to deliver substances at respective received controlled delivery rates to respective animals (e.g., one animal per pump). In some embodiments, the computer system may also send/receive other information to/from the pumps (e.g., to control various aspects of the pumps and/or store information associated with the pumps). In some embodiments, the computer system may determine respective controlled delivery rates for the pumps based in part on a weight of a respective animal receiving the substance from the respective pump and/or for example, a study group the animal is in. For example, a study may involve testing one group of animals with a high dose of a substance, one group with a mid dose of the substance, one group with a low dose of the substance, and one group with a control substance (other study configurations are also contemplated). In some embodiments, the computer system may calculate and then send the determined controlled delivery rates to the respective pumps in response to a global command (e.g., received from an operator). The pumps may use the received determined controlled delivery rates to control the rate of substance delivery to a respective animal that is receiving the substance from the respective pump (e.g., through an intravenous (IV) connection to a syringe with the substance being controlled by the pump). In some embodiments, the computer system may display respective graphical profiles of the controlled delivery rates over time for the respective pumps. The graphical profiles may also include indicators marking the graphical profile at the current time point in the study.

In some embodiments, pumps and other equipment (e.g., medical or monitoring devices) may communicate with the computer system through wired and/or wireless connections. For example, the connections may form a mesh network allowing the computer system to send and receive information to the pumps and other equipment. In some embodiments, the computer system may communicate with the pumps and other equipment through a data hub. In some embodiments, the pumps and other equipment may be coupled to a box operable to send/receive communications to/from the network. The boxes may also include memory for storing information such as instructions (e.g., for the pump), a controlled delivery rate, a start time, a stop time, a duration, a target volume, etc. to allow the box to provide the instructions, etc. in the event of a computer system failure and/or to allow the box to be placed on a different pump if the original pump should fail (or for some other reason need to be disconnected from the study).

In some embodiments, the computer system may receive information such as weights (e.g., from a weight scale, file, or remote computer), sensor data (e.g., from monitoring sensors either implanted in the animals or coupled to cages holding the animals), documentation (e.g., including user identifiers and documentation identifiers for respective events occurring in the network such as pump starting, pump stopping, alarm, alarm cleared, how alarm was cleared, etc). User identifiers (e.g., personal identification numbers (PINs)) may be used to authenticate an operator prior to allowing the operator to perform an action on the pump (or other equipment). The user identifier may also be stored with a received documentation identifier to indicate which operator performed the respective action. In some embodiments, user identifiers and documentation indicators (e.g., when clearing an alarm) may be required prior to continued system access and/or prior to restarting pump operation (e.g., if stopped after an alarm).

In some embodiments, the computer system may communicate with the pumps and/or weight scales associated with the pumps for in process pump validation. For example, an operator may weigh a syringe before a pump pumps a substance and after the pump pumps the substance according to a received controlled delivery rate. The weights (and, for example, start and stop times) may be used to validate the pump (e.g., determine if the expected delivery rate is within an acceptable range of the actual delivery rate (output volumes may also be used in the validation)). The computer system may also track calibration dates for the pumps and may warn an operator (or, for example, inhibit pump operation) of pumps that have gone past their calibration intervals (or will go past their calibration intervals during the study).

In some embodiments, the computer system may communicate with a filling pump (either coupled or not coupled to an animal) to fill syringes with an amount of substance needed for a next phase of a study. For example, after determining a controlled delivery rate for a pump (and a duration of pumping at the determined controlled delivery rate), the computer system may determine and communicate an amount of substance needed in a respective syringe (or, for example, a syringe plunger displacement indication, etc.) to a filling pump and the filling pump may fill the respective syringe with the indicated amount of substance (the syringe and a vat of the substance to be used to fill the syringe may be coupled to the filling pump by an operator). An indicator (e.g., printed directly on the syringe or on a label to be coupled to the syringe) may be placed on the syringe to assist the operator in placing the syringe on the respective pump (in some embodiments, the same pump may fill the syringe and deliver the substance to the respective animal). In some embodiments, the computer system may calculate several syringe amounts and may display (or, for example, print) the list for an operator to use in preparing syringes for future phases of the study (e.g., the list may include entries with a pump indicator, a time indicator, an amount indicator, an animal indicator, etc. along with the substance amount to fill the respective syringe with). In some embodiments, when a syringe is placed into a pump, the pump (e.g., using information stored in the box and/or received from the computer system) may check a diameter of the received syringe to make sure the received syringe diameter corresponds to the expected syringe diameter (different sized syringes may be used at different times in the study). In some embodiments, the pump may indicate an error and/or not pump the syringe if the diameters do not match.

BRIEF DESCRIPTION OF THE DRAWINGS

A better understanding of the present invention may be obtained when the following detailed description is considered in conjunction with the following drawings, in which:

FIG. 5 illustrates an embodiment of monitoring devices for monitoring the micro-environments of multiple animal cages in a rack and cage system.

FIG. 9 illustrates a set-up screen for a study, according to an embodiment.

FIG. 10 illustrates a security set-up screen, according to an embodiment.

FIG. 12 illustrates a user set-up screen, according to an embodiment.

FIG. 15b illustrates a listing of future syringes, according to an embodiment.

Figure 1:
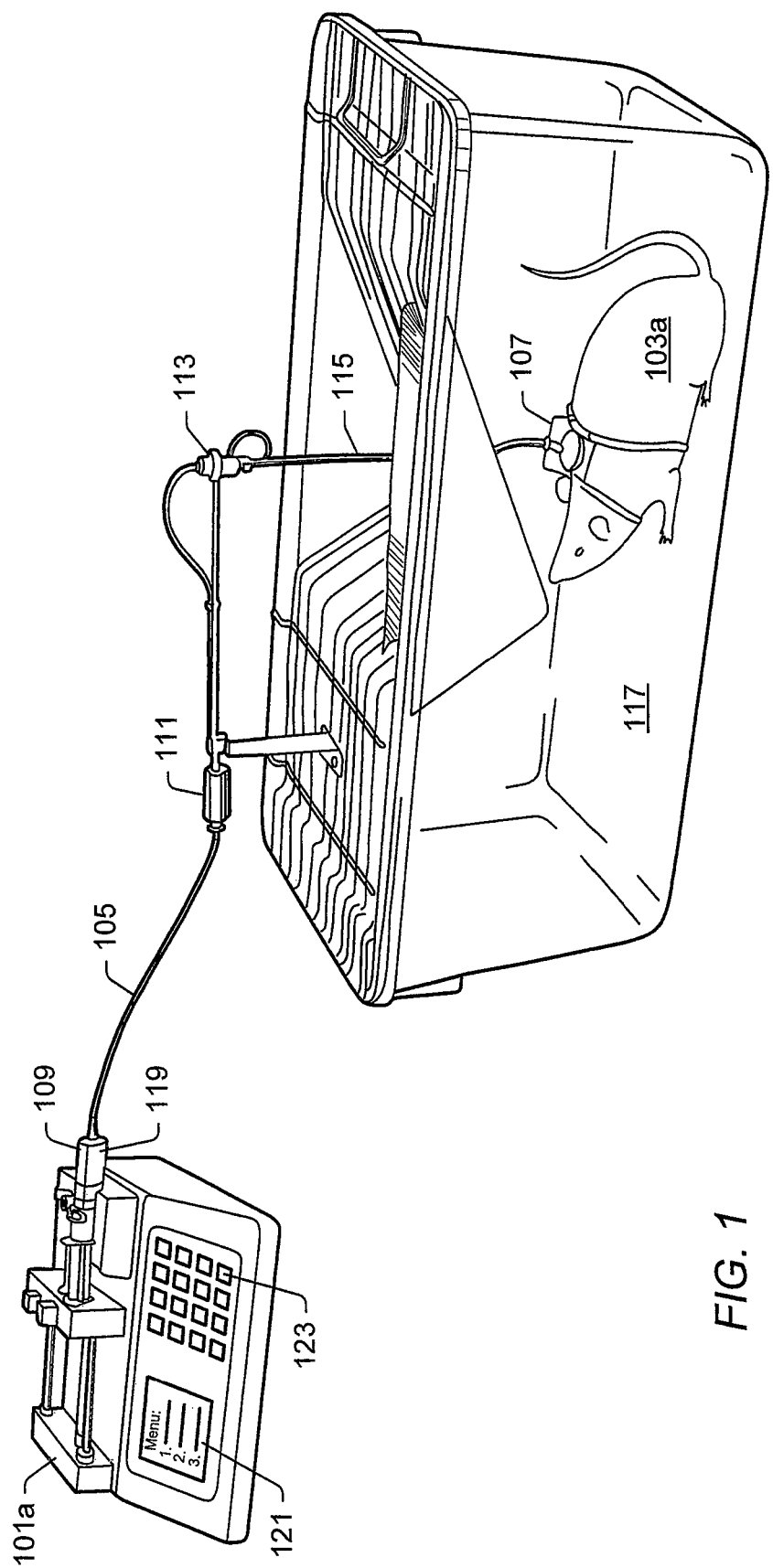
FIG. 1 illustrates a pump and an animal cage, according to an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims. Furthermore, note that the word "may" is used throughout this application in a permissive sense (i.e., having the potential to, being able to), not a mandatory sense (i.e., must). The term "include", and derivations thereof, mean "including, but not limited to". The term "coupled" means "directly or indirectly connected".

DETAILED DESCRIPTION OF THE EMBODIMENTS

FIG. 1 illustrates an embodiment of pump 101a (e.g., a medical infusion pump) and a laboratory animal cage 117 for animal 103a. In various embodiments, pump 101 ("pump 101" used generally herein to refer to pumps 101a, 101b, 101c, etc.) may be used to deliver substance 119 to animal 103 ("animal 103" used generally herein to refer to animals 103a, 103b, 103c, etc.) at a controlled delivery rate (e.g., to study the effects of substance 119 on respective animal 103). In some embodiments, the controlled delivery rate may be calculated, for example, by computer system 201 (e.g., see FIG. 2) and communicated to pump 101 for use in delivering substance 119 to animal 103. As discussed herein, other information may also be communicated between computer system 201, pumps 101, and other equipment in an animal drug study. While embodiments described herein include animal applications (e.g., laboratory/veterinary research applications), other applications are also contemplated (e.g., human study applications).

In some embodiments, pump 101 may include a stepper motor to push a plunger on syringe 109 to deliver substance 119 in syringe 109 at the controlled delivery rate (or pull the plunger to load substance 119 into syringe 109). While syringe 109 is used throughout, other delivery containers (e.g., a holding tank) are also contemplated. Other pump types are also contemplated (e.g., peristaltic, diaphragm, large volume, stationary ("pole mount"), and portable ("ambulatory")). Animals 103 may include rodents, pigs, rabbits, dogs, cats, nonhuman primates, etc. Substances 119 may include a saline solution, a drug solution, or a control solution (which may be a saline solution). Other substances 119 are also contemplated. In some embodiments, substance 119 may be a liquid delivered through tube 105 on animal 103 which may deliver substance 119 intravenously (through a catheter 107) to animal 103. Other routes of administration are also contemplated. For example, substance 119 may be an airborne particle that is pumped into an animal's breathing space or a solid/liquid substance that is pumped into the animal's digestive system. Substance 119 may also be applied to the animal's eyes, ears, skin, etc. (e.g., by a spray pump). In some embodiments, counter balance 111, swivel 113, and spring tether 115 may be used to guide and stabilize tube 105 transporting substance 119 to animal 103 in animal cage 117. Other configurations are also contemplated.

Figure 2A:
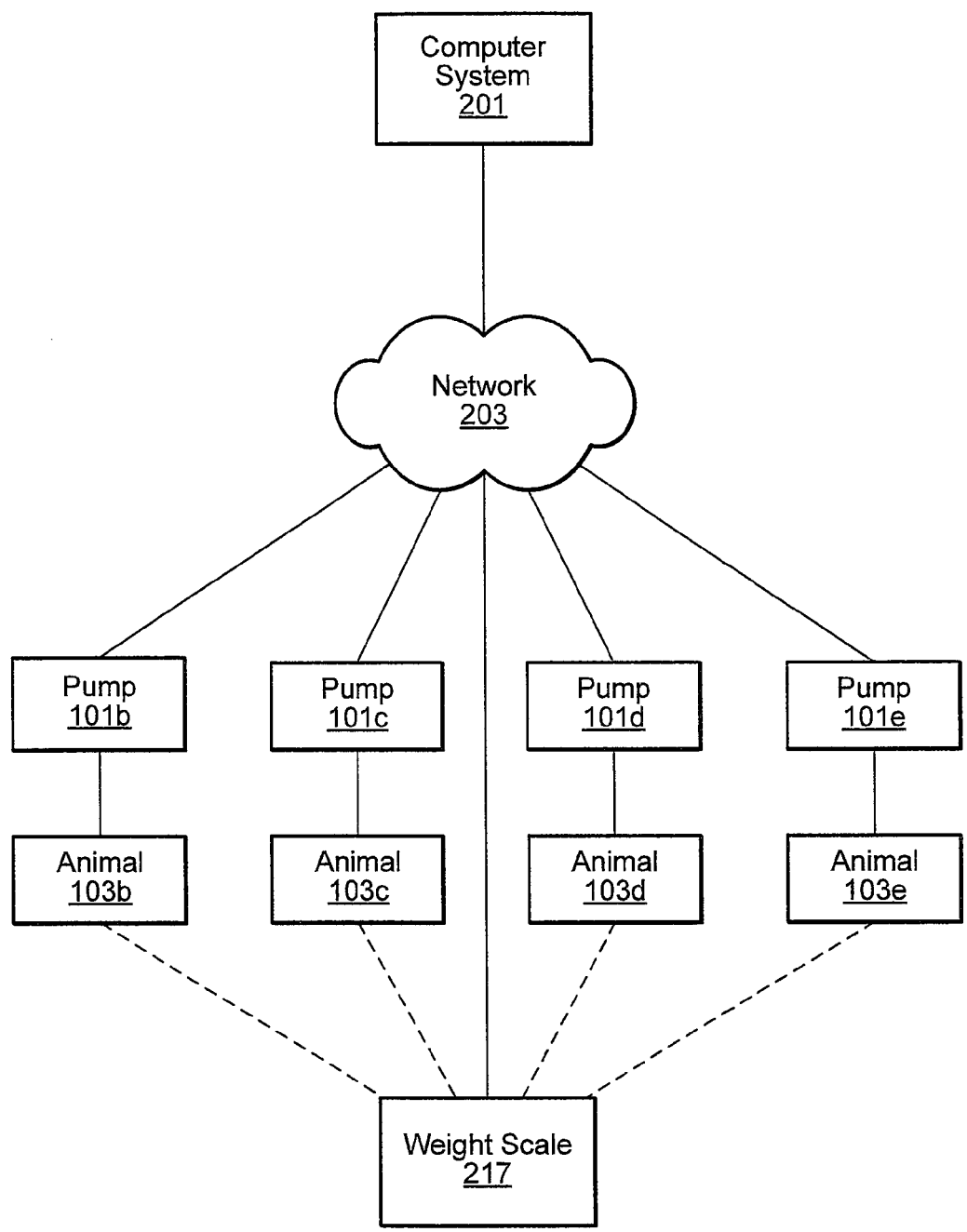
FIG. 2a illustrates multiple pumps communicating with a computer system, according to an embodiment.

FIG. 2a illustrates multiple pumps 101 communicating with computer system 201, according to an embodiment. In some embodiments, multiple pumps 101 (e.g., pumps 101b, 101c, 101d, and 101e) may be used to deliver substances 119 to multiple respective animals 103 (e.g., animals 103b, 103c, 103d, and 103e). For example, a toxicity study may include delivering different respective amounts of a drug to different animals (e.g., one animal 103 per pump 101) to determine the toxic effects (if any) of the drug and to determine ideal drug amount/body weight ratios. Other study types and study characteristics (e.g., effects of the drug on different genders, age groups, etc.) are also contemplated. Studies may require testing tens, hundreds, or thousands of animals over a few hours, days, weeks, etc. Animal studies may be preliminary to human studies (e.g., for obtaining FDA approval). For example, animal studies may be used in researching new formulations for drugs to treat diseases (e.g., heart disease, diabetes, etc.)

In some embodiments, pumps 101 may communicate with computer system 201 through network 203 (e.g., through wired and/or wireless communications). Computer system 201 may be a personal computer (such as a desktop or laptop), mainframe, etc. Other computer system types are also contemplated. In some embodiments, computer system 201 may include several computer systems communicatively coupled together. In some embodiments, computer system 201 may send/receive information to/from pumps 101 and other equipment involved in the study (e.g., medical or monitoring devices such as weight scale 217). For example, computer system 201 may receive weight data from weight scales 217 to determine, for a respective pump 101, a respective controlled delivery rate for delivering substance 119 to animal 103. Computer system 101 may then send the determined controlled delivery rate to the respective pump 101. Each animal 103 may have an individual weight scale 217 (e.g., incorporated in respective animal cage 117) or multiple animal cages 117 may share a weight scale 217. In some embodiments, weight scale 217 may communicate (e.g., measured animal weights) with computer system 201 through network 203.

In some embodiments, computer system 201 may provide an interface for operator 401 (e.g., see FIG. 4) to automate control of pumps 101 and the other equipment involved in the study. Information may also be received at computer system 201 from pumps 101 and other equipment (e.g., other medical or monitoring devices) communicatively coupled to computer system 201. For example, information may be entered at pump 101 through an operator interface 123 (e.g., an alpha/numerical keypad, a full Qwerty keyboard, etc). In some embodiments, information may also be displayed on pump display 121 (e.g., see menu displayed on display 121 in FIG. 1). Other pump configurations are also contemplated. Computer system 201, pumps 101, and/or other medical or monitoring devices may also be operable to communicate (e.g., send and receive data and instructions) with personal digital assistants (PDAs), cell phones, smart cards, etc. For example, operator 401 may send information to computer system 201 through a PDA (e.g., an animal weight, documentation of a study event, etc). As another example, operator 401 may send information to pump 101 by entering the information into a PDA; the PDA sending the information to computer system 201, and the information being transmitted to pump 101 from computer system 201 over network 203. As another example, operator 401 may send information to computer system 201 by entering the information into a PDA; the PDA sending the information to pump 101, and the information being transmitted to computer system 201 from pump 101 over network 203. Computer system 201 may be used by operator 401 to set-up a study (e.g., by calculating respective controlled delivery rates) and automate documentation for the study (e.g., associated with pumps 101 and the other equipment involved in the study). Automating control may save substantial time over manual pump set-ups. In addition, automating documentation may result in more accurate and complete study documentation (often required by the FDA and other regulatory bodies) and may force operators 401, etc. to enter documentation at the appropriate times (e.g., during a pump alarm).

In some embodiments, computer system 201 may determine respective controlled delivery rates for substance delivery for pumps 101 (e.g., based in part on a weight of animal 103 receiving substance 119 from respective pump 101) and send the determined controlled delivery rates to respective pumps 101. In some embodiments, controlled delivery rates may include [dose/time]/animal weight ([ml/hr]/kg) where dose may indicate a substance concentration. Other controlled delivery rates are also contemplated (e.g., non-weight based controlled delivery rates may include dose/time (ml/hr)). Pumps 101 may use the received determined controlled delivery rate to control the rate of substance delivery to animal 103 that is receiving substance 119 from respective pump 101.

In some embodiments, studies may involve testing groups of animals with different levels of drug doses. For example, a study may involve testing one group of animals with a high dose of substance 119, one group with a mid dose of substance 119, one group with a low dose of substance 119, and one group with a control (other study configurations are also contemplated). In some embodiments, computer system 201 may also use the study group criteria in determining the respective controlled delivery rate for pump 101 (e.g., in addition to the determined animal weight). Pumps 101 in the high dose group may be provided a controlled delivery rate with an increased dose of the drug per unit of body weight than the mid or low dose group pumps 101. In some embodiments, study ratios (of substance amount per unit body weight) may be provided to computer system 201 (e.g., by operator 401) for each group along with a number of animals 103 to test in each dose group (or a respective percentage of the total number of animals to include in each group). For example, operator 401 may provide a spreadsheet with the ratios (and, for example, other test parameters such as animal type, gender, age, etc.) to computer system 201. Other information may also be received (e.g., time periods for administering the drugs). Other sources of the study information are also contemplated (e.g., downloaded from a remote computer). Computer system 201 may use this information to set up which pumps 101 will provide which dose levels. The respective weights of the animals may also be received by computer system 201 (e.g., on a spreadsheet, through manual entry on a pump interface 123, through a weight received from weight scale 217 associated with pump 101, etc). Computer system 201 may arrange pump groupings (e.g., by assigning pumps 101 to respective groups), pump controlled delivery rates, etc. and communicate the resulting respective controlled delivery rates to respective pumps 101 throughout the study.

Figure 2B:
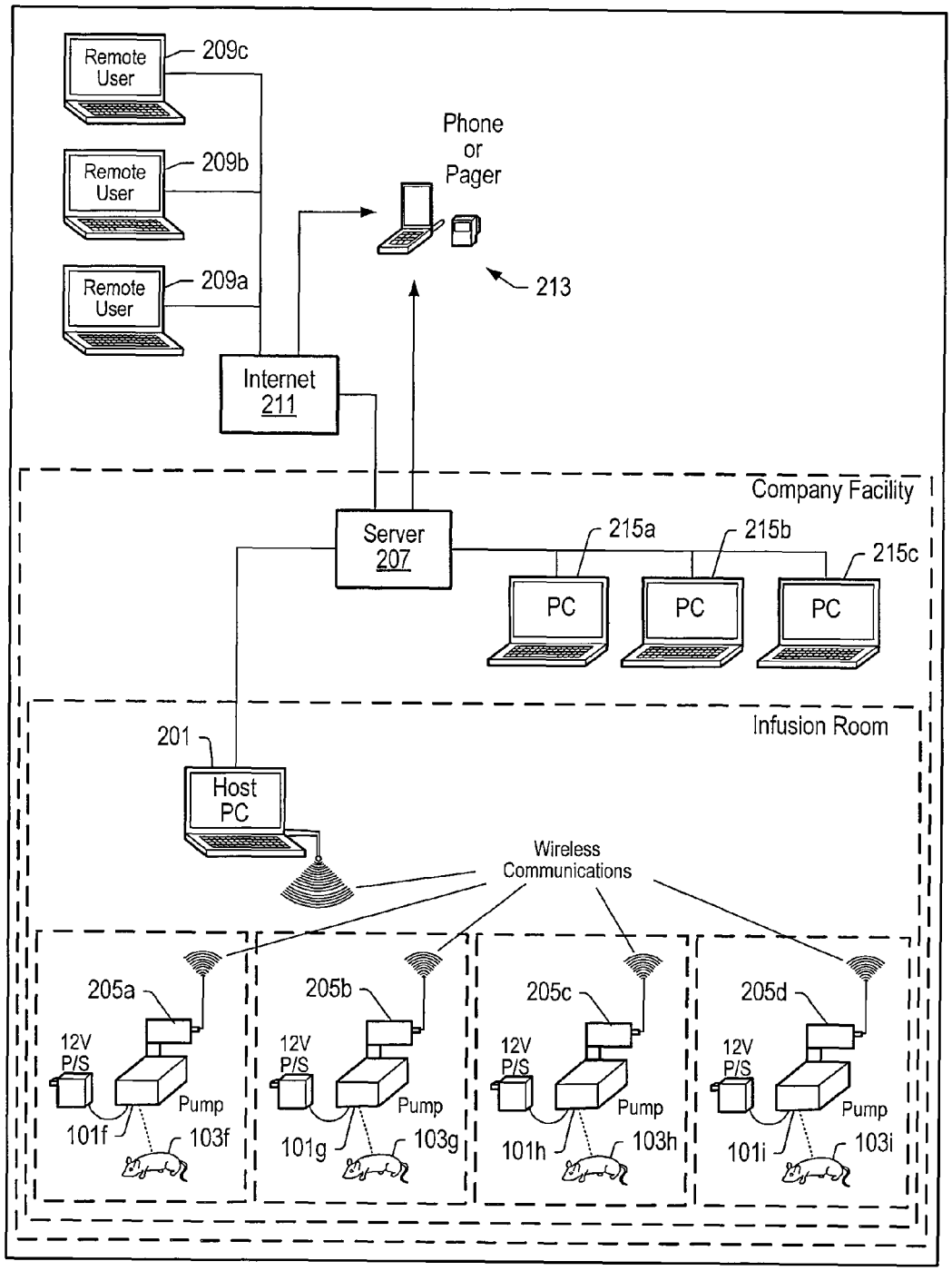
FIG. 2b illustrates multiple pumps communicating with a computer system through respective boxes, according to an embodiment.
Figure 3:
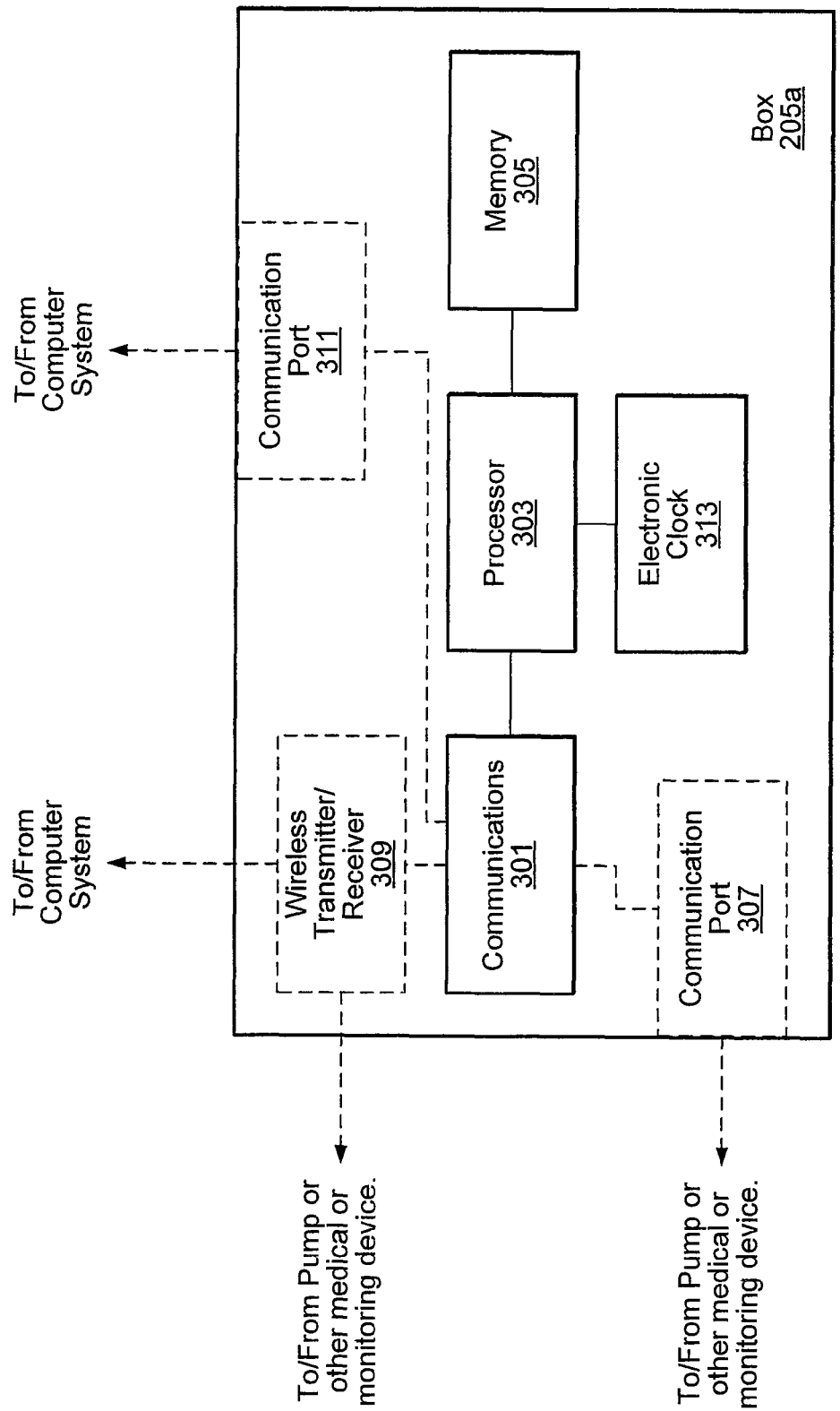
FIG. 3 illustrates a box, according to an embodiment.

In some embodiments, pumps 101 and/or other medical or monitoring devices may communicate over network 203 with computer system 201 through wired and/or wireless communications. For example, pumps 101 (e.g., pumps 101f, 101g, 101h, and 101i) and/or other medical or monitoring devices may include and/or be coupled to wireless communication devices such as Wireless Fidelity (IEEE 802.11b wireless networking) (Wi-Fi) transmitter/receiver, Bluetooth transmitter/receiver), etc. for communication with computer system 201. In some embodiments, pumps 101 and/or other medical or monitoring devices (e.g., as seen in FIG. 2b) may communicate with computer system 201 through boxes 205 (e.g., see boxes 205a, 205b, 205c, and 205d (referred to generally herein as boxes 205)). In some embodiments, box 205 attached to a communication port of pump 101 and/or other medical or monitoring devices (e.g., through communication port 307 as seen in FIG. 3) may send/receive information to/from pump 101 (and/or other medical or monitoring devices) and computer system 201 (e.g., wirelessly through wireless transmitter/receiver 309 or through a wired connection through communication port 311). In some embodiments, box 205 may not be physically attached to pump 101 and/or other medical or monitoring devices, but may communicate with pump 101 and/or other medical or monitoring devices through wireless transmitter/receiver 309 (which may include a separate transmitter and receiver or a transceiver). Other communication configurations are also contemplated. As seen in FIG. 2b, pumps 101f, 101g, 101h, and 101i may use respective controlled delivery rates received from computer system 201 to pump the determined respective amounts of substance 119 into animals 103f, 103g, 103h, and 103i.

In some embodiments, pumps 101 and/or other medical or monitoring devices may also be coupled to computer system 201 through wired connections (in some embodiments, boxes 205 may provide wired and/or wireless connections). In some embodiments, pumps 101 and/or other medical or monitoring devices may have communication ports (e.g., serial RS-232, Universal Serial Bus (USB), Ethernet, other communications (COM) port, etc). Connections may be made through the communication ports directly to computer system 201 (e.g., through a wired connection) or indirectly to computer system 201 (e.g., box 205 may be coupled to the communication port and may send/receive communications to/from computer system 201 through a wired and/or wireless connection). Other connections are also contemplated.

In some embodiments, network 203 may be a mesh network. Through the mesh network, pumps 101 (and, for example, other medical or monitoring devices) in network 203 may communicate directly with each other and/or communicate with each other via computer system 201. For example, computer system 201, boxes 205, etc. may use a ZigBee™ wireless protocol for peer-to-peer communication (which may provide alternate communication paths in the network 203 if a direct path is not available). In some embodiments, computer system 201, boxes 205, etc. may communicate with each other through a router. In some embodiments, the router may be external or internal to computer system 201. Other network configurations and protocols are also contemplated.

In some embodiments, pump 101 may access memory 305. Memory 305 may be internal to pump 101 or may be external to pump 101 (e.g., memory 305 may be in box 205 communicatively coupled to pump 101). Memory 305 may include a non-volatile memory (e.g., flash memory) or volatile memory (e.g., Random Access Memory (RAM)). Other memory types are also contemplated. In some embodiments, memory 305 may store information such as instructions (e.g., for pump 101), a controlled delivery rate, a start time, a stop time, a duration, a target volume, etc. for pump 101 from computer system 201. For example, memory 305 may store the received controlled delivery rate, a start time, and a duration from computer system 201 for pump 101 to use in pumping substance 119 to animal 103. Other combinations are also contemplated (e.g., memory 305 may store controlled delivery rate and target volume or controlled delivery rate and a start and stop time). Memory 305 may also include program instructions (e.g., received from computer system 201) to control pump 101. For example, the programming instructions may be stored as firmware on memory 305. Because instructions for pump 101 may be stored on memory 305, if computer system 201 fails (or, for example, is restarted, disconnected, etc.), pumps 101 may continue operation per the instructions stored on memory 305. In some embodiments, programming instructions for determining the controlled delivery rate for pump 101 may be stored in memory 305. The controlled delivery rate may be determined based on information collected at pump 101 and corresponding information may be sent to computer system 201 for storage (e.g., the animal's weight, the controlled delivery rate, etc). In some embodiments, computer system 201 may communicate information needed for the calculation to pump 101 and/or box 205 (e.g., a dose ratio assigned to respective pump 101) to be used with the programming instructions on memory 305 and/or other data in memory 305 for the calculation. Memory 305 may also include, for example, alarm codes, menu options for indicating how alarms were solved, etc. Memory 305 may also store information sent to and received from computer system 201 (e.g., as serve as a back-up for computer system 201). In some embodiments, memory 305 may be accessible to other medical or monitoring devices (e.g., internal to the devices or externally accessible to the devices) for storing information (e.g., information sent/received to/from computer system 201) and/or instructions for these devices. For example, box 205 with memory 305 may be coupled to a medical or monitoring device's communications port. In addition to memory 305, box 205 may include processor 303 to access memory 305, electronic clock 313, and communications circuitry 301. In some embodiments, the memory 305 and wireless transmitter/receiver 309 may be on the same printed circuit board (PCB). Other configurations are also contemplated. In some embodiments, memory 305 may be included in a router (e.g., external to computer system 201) to allow continued operation of pumps 101, medical and monitoring devices, network 203, etc. if computer system 201 fails (or, for example, is restarted, disconnected, etc).

In some embodiments, box 205 may be replaced on pump 101 (and/or other medical or monitoring device) (e.g., if box 205 fails, is not functioning properly, is being updated, etc). For example, an external box 205 may be replaced without replacing or repairing pump 101 (and/or other medical or monitoring device). If the memory 305 and/or communications circuitry 301 is on box 205 instead of an interior of pump 101, the memory 305 and communications circuitry 301 may be easier to repair/replace by replacing box 205 (as opposed to accessing the interior of pump 101). In some embodiments, if pump 101 (or other medical or monitoring device) fails, is not functioning properly or, for example, is being updated, box 205 may be placed on a different pump 101 (or other medical or monitoring device). In some embodiments, box 205 may not need to be reprogrammed after the switch (e.g., box 205 may interact with the new pump to perform the functionality expected of the previous pump (e.g., controlled delivery rate, delivery schedule, etc)). In some embodiments, box 205 may be configured to interface with different types of pumps 101 (and/or other medical or monitoring device). Box 205 may include dedicated programming instructions specific to the pump style (or style of other medical or monitoring device). In some embodiments, the pump 101 (and/or other medical or monitoring device) may include programming instructions to be compatible with box 205. In some embodiments, box 205 may be internal to pump 101 (and/or medical or monitoring device) and pump 101 (and/or medical or monitoring device) may be repaired or replaced if the internal box 205 is not functioning properly (or, for example, to update box 205). In some embodiments, box 205 may include a wireless communications device with one or more communication port connectors (e.g., serial RS-232, USB, Ethernet, etc) to configure box 205 to communicate with a specific pump 101. In some embodiments, communications circuitry 301 (and, for example, wireless transmitter/receiver 309, communication ports 307/311) processor 303, memory 305, and/or electronic clock 313 may be internal to pump 101 (and/or medical or monitoring device). Other placements are also contemplated.

Figure 4:
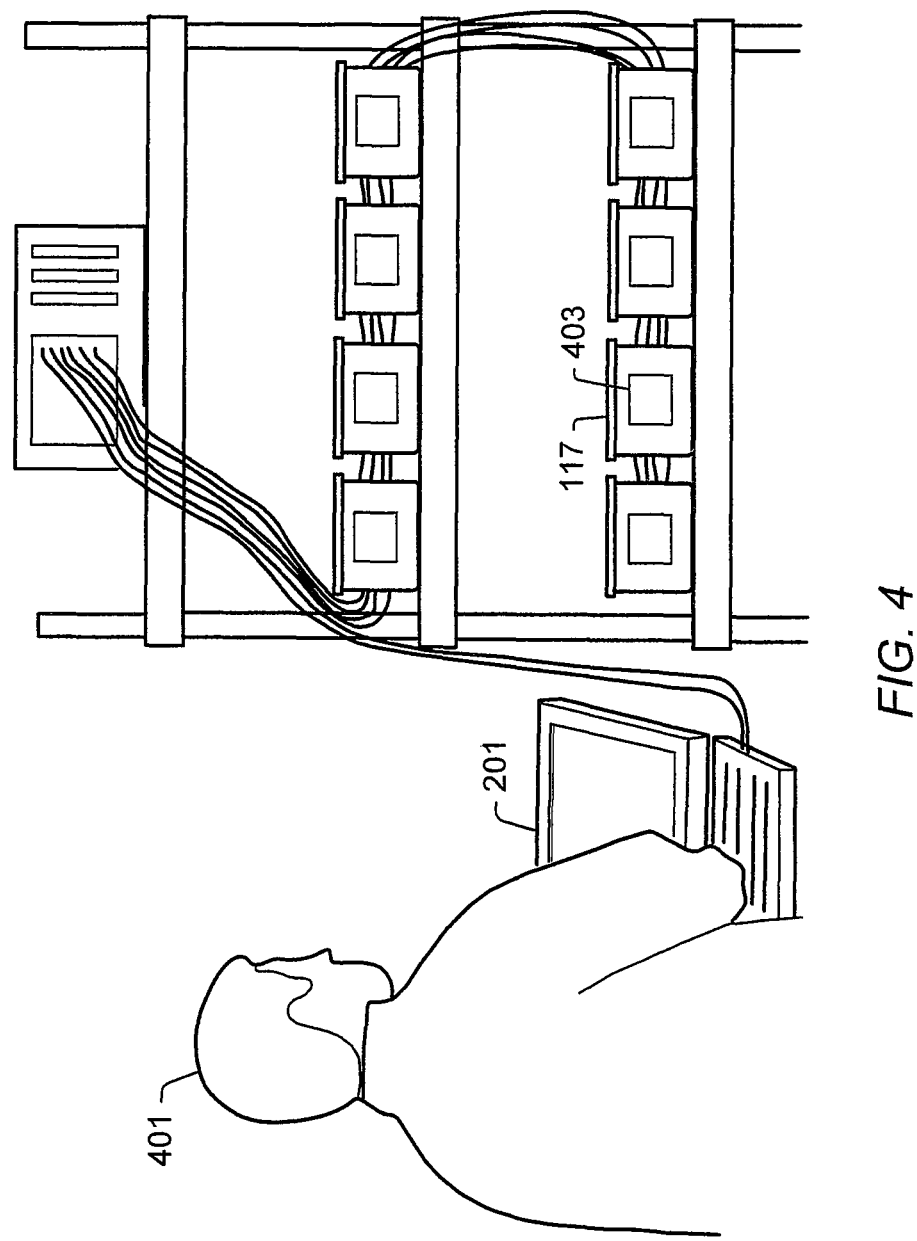
FIG. 4 illustrates a food consumption monitoring device, according to an embodiment.

In some embodiments, other medical or monitoring devices (e.g., used to treat or monitor humans or animals 103) may communicate with computer system 201. For example, the medical or monitoring devices (e.g., sensors) may monitor physiologic parameters (e.g., animal temperature, activity, pulse oximetry, heart rate, blood pressure, metabolic function, etc) and animal cage conditions (e.g., a micro-environment monitoring apparatus may measure animal cage temperature, humidity, ammonia level, etc)). As seen in FIG. 4, a monitoring device may include a food and/or water consumption monitoring device 403 (e.g., for one animal cage 117 of a collection of animal cages). In some embodiments, network 203 may include individual laboratory animal cages 117 with respective devices for monitoring the weight of feed dispensed (and, in some embodiments, consumed) (e.g., food consumption monitoring device 403) by animal 103 (e.g., a rat) in the respective animal cages 117 (e.g., separate monitoring devices for each of the respective animal cages 117). FIG. 5 illustrates an embodiment of monitoring devices for monitoring the micro-environments of multiple animal cages 117 in a rack and cage system 405. The medical or monitoring device may include a rack and cage system 405 including multiple laboratory animal cages 117 and micro-environment monitoring devices attached to respective animal cages 117 to measure conditions within each animal cage 117 (e.g., temperature, humidity, etc). This micro-environment data may be transmitted to computer system 201 (e.g., wirelessly through communications circuitry in the monitoring devices or box 205 coupled to the monitoring devices).

In some embodiments, medical or monitoring devices may include weight scale 217 used to determine a weight of animal 103, cage 117, etc. Other weight determinations are also contemplated (e.g., the weight of a syringe for pump 101 may be weighed in weight scale 217 for transmission to computer system 201). In some embodiments, computer system 201, weight scale 217 (and/or other medical or monitoring devices), and pump 101 may form a closed information loop. Other information arrangements are also contemplated. Other medical or monitoring devices are also contemplated (e.g., a Wireless Information Device (WID) reader for animal identification based on an implanted, external, and/or wearable Radio Frequency Identification (RFID) chips) may be used to identify specific animals associated with a specific animal cage 117 (e.g., with the reader). Medical or monitoring devices may thus include monitoring sensors either implanted in animals 103 or coupled to cages 117 holding animals 103. Medical or monitoring devices may transmit and receive information to/from computer system 201 (e.g., through wired and/or wireless communications). In some embodiments, pumps 101 (and/or medical or monitoring devices) in network 203 may have unique addresses (e.g., unique Internet protocol (IP) addresses). Other unique address types are also contemplated (e.g., Media Access Control (MAC) addresses). In some embodiments, computer system 201 may use the unique addresses to send/receive information to/from pumps 101 (and/or medical or monitoring devices) to control, monitor, and/or store information associated with pumps 101 (and/or medical or monitoring devices).

In some embodiments, computer system 201, pumps 101 (and/or other medical or monitoring devices) may communicate with other computers (e.g., via an intranet or Internet 211). For example, information from computer system 201 may be sent to server 207 in communication with remote personal computers 209 (e.g., computers 209a, 209b, and 209c) over Internet 211. In some embodiments, a network of remote computers may communicate with computer system 201 for remote access to data in computer system 201 (e.g., remote computers 209 may communicate with computer system 201 via Internet 211 and/or via server 207 coupled to and/or including computer system 201). In some embodiments, other remote computers 215 (e.g., computers 215a, 215b, and 215c) may access computer system 201 through server 207. Remote access may allow operators 401 (e.g., remote operators) to monitor and/or control equipment in the study, access documentation, etc. Other uses for remote access are also contemplated. In some embodiments, computer system 201 may notify an entity (e.g., operator 401) of the status (e.g., normal or abnormal) of pumps 101 and/or medical or monitoring devices and may allow the entity to control pumps 101 and/or medical or monitoring devices communicating through network 203. In some embodiments, computer system 201 may notify operator 401 via electronic mail messages, text messages, paging, voice messaging, etc. of a status and, for example, may receive control instructions through operator mobile device 213 (e.g., a phone, PDA, etc.).

In some embodiments, computer system 201 may communicate through wired, wireless, or a combination of wired and wireless network hardware to pumps 101 and/or medical or monitoring devices to program, monitor, and collect data from the pump 101 and/or medical or monitoring devices. The network combinations may include, for example, a data hub communication arrangement (e.g., see FIG. 6), a rack hub communication arrangement (e.g., see FIG. 7), a box communication arrangement (e.g., see FIG. 8), or various subsets and/or combinations of these communication arrangements (other network configurations are also contemplated).

Figure 6:
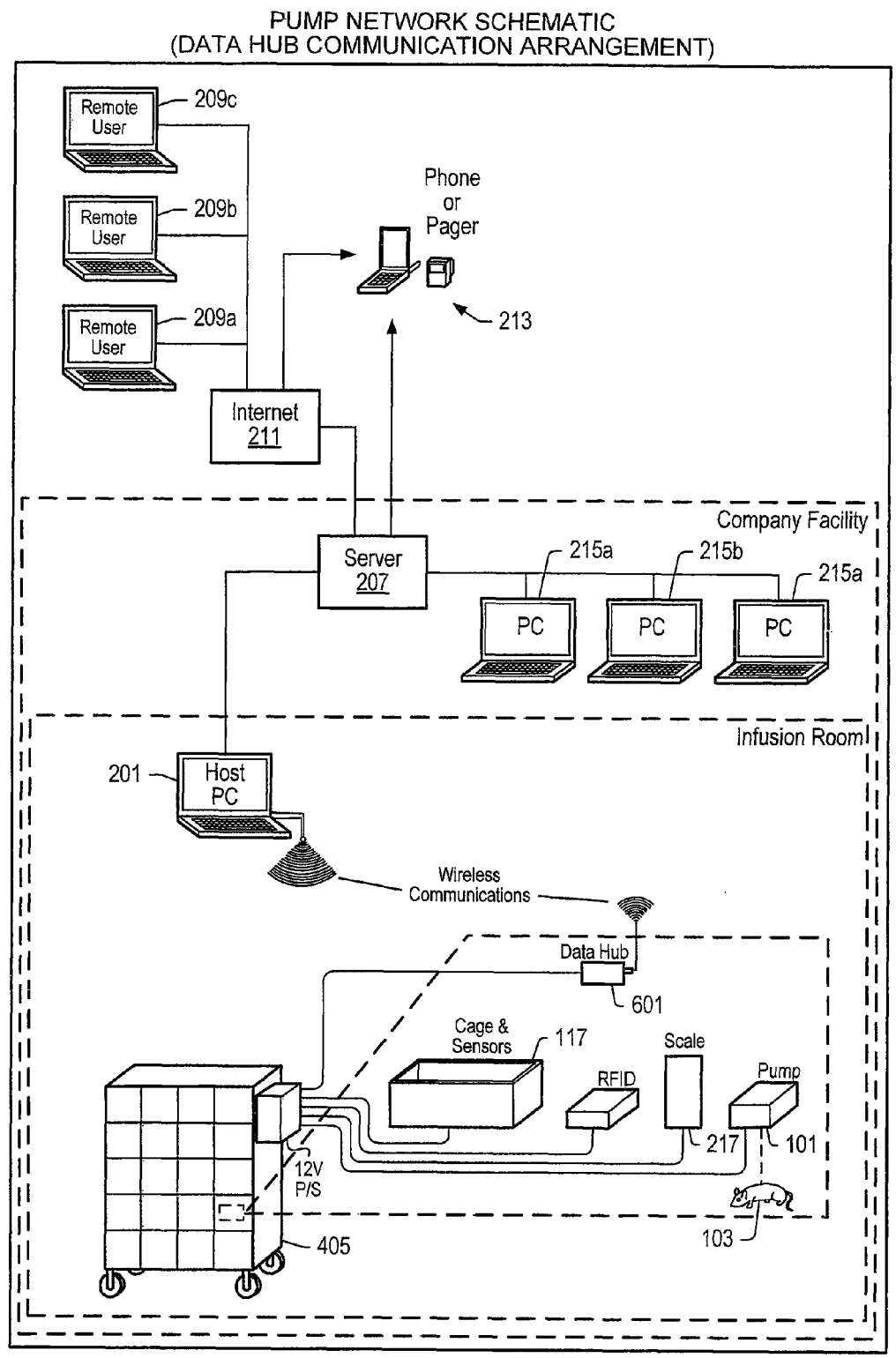
FIG. 6 illustrates a data hub communication arrangement including a pump and medical and monitoring devices wired to an external stand-alone data hub, according to an embodiment.
Figure 7:
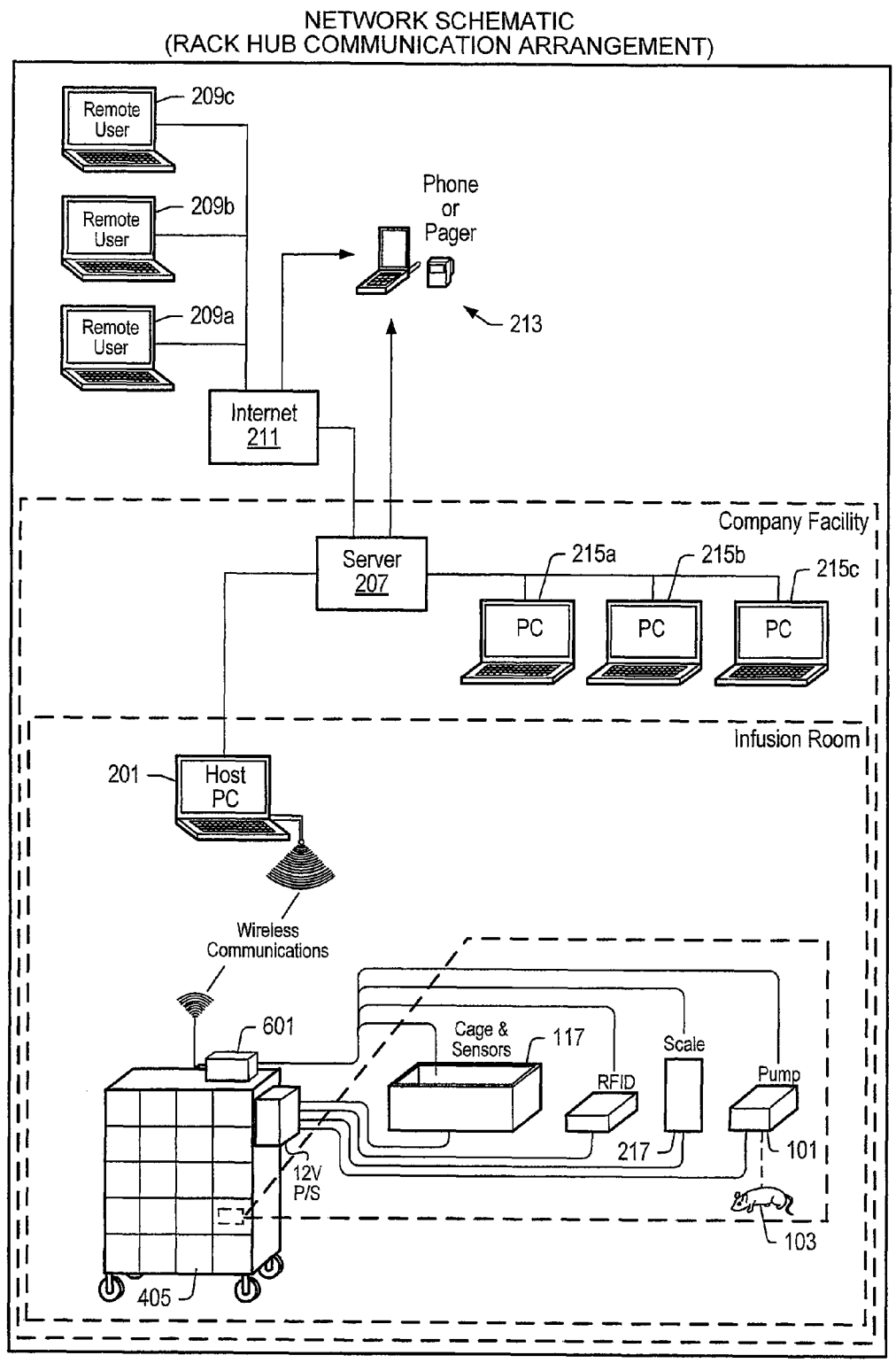
FIG. 7 illustrates a rack hub communication arrangement with multiple pumps and medical and monitoring devices in a rack wired to an external stand-alone data hub, according to an embodiment.

FIG. 6 illustrates an embodiment of the data hub communication arrangement including pump 101 and/or medical or monitoring devices wired (or wirelessly connected) to data hub 601 (e.g., an external stand-alone data hub). FIG. 6 illustrates an embodiment including rack 405 with multiple cages 117, integrated direct current (DC) power ports, and a universal, removable power supply (other configurations are also contemplated). FIG. 7 illustrates an embodiment of a rack hub communication arrangement with multiple pumps 101 and/or medical or monitoring devices in rack 405 wired or wirelessly connected to data hub 601 (e.g., an external stand-alone data hub mounted to rack 405). FIG. 7 illustrates an embodiment of rack 405 with multiple cages 117 and a mounted data hub 601 operable to handle the infusion groups within the single rack 405 (other configurations are also contemplated). In some embodiments, cage rack 405 may also include integrated washable DC power ports and a Universal, removable power supply. Other data hub types and placements are also contemplated. The data hub hardware may include embedded programming instructions operable to allow data input to/from multiple devices (e.g., pump 101 and/or medical or monitoring devices (such as sensors and weight scales), etc.) and to/from computer system 201. Data hub 601 (e.g., a universal data hub) may be placed on, in or proximate to animal cage 117, pump 101, and/or medical or monitoring device (e.g., one data hub 601 per animal cage 117, one data hub 601 per pump 101, one data hub 601 supporting multiple animal cages 117 in rack 405, etc). In some embodiments, a single data hub 601 may be located at each of one or more animal cages 117. In some embodiments, a single data hub 601 may be coupled to multiple animal cages 117 (e.g., coupled to rack 405). Other configurations are also contemplated. In some embodiments, pump 101 and/or medical or monitoring devices dedicated to animal cage 117 may communicate bi-directionally with data hub 601 and to computer system 201 (e.g., through data hub 601).

In some embodiments, data hub 601 may accommodate multiple wired and/or wireless data platforms and protocols used in pumps 101, and/or medical or monitoring devices (e.g., Ethernet, RS232, USB, Wi-Fi, Bluetooth, etc). For example, data hub 601 may pass through (and/or convert) communications to/from pumps 101 and/or medical or monitoring devices to/from computer system 201. In some embodiments, data hub 601 may integrate multiple data sources from pumps 101 and/or medical or monitoring devices into a data stream for transmission to computer system 201 (e.g., wirelessly). In some embodiments, data hub 601 may multiplex various communications from pump 101 and/or medical or monitoring devices to computer system 201. Computer system 201 may separate the data streams (e.g., using a pre-arranged template shared with data hub 601 and/or a demultiplexer). Other communication formats are also contemplated (e.g., data to/from pump 101 and/or medical or monitoring devices may be transmitted/received as single serial streams). Computer system 201 may transmit information intended for pump 101 and/or medical or monitoring devices to data hub 601 for delivery to the intended pump 101 and/or medical or monitoring devices (these streams may also be combined/multiplexed streams or separate streams). In some embodiments, data hub 601 may support a generic platform to transmit and receive data to/from several different types of platforms (e.g., different pump types, different computer systems, etc). In some embodiments, data hub 601 may include programming instructions to convert data in one platform to another platform prior to sending the data to an intended device.

In some embodiments, data hub 601 may transmit bi-directional data for a single animal cage 117 to computer system 201 (e.g., via wired or wireless hardware) or data hub 601 may transmit bi-directional data for animal cages 117 in rack 405 to computer system 201 (e.g., via wired or wireless hardware). In various embodiments, a lab animal cage rack 405 (other rack types are also contemplated) may hold multiple animal cages 117 (e.g., 10, 100, 1000, etc). The cage rack 405 may include power sources 603 (which may be integrated in the cage rack 405) and wires as well as data communication devices and wires for pumps 101 and/or medical or monitoring devices on animal cages 117. In some embodiments, power sources 603, wires, communication devices, etc. may be removable and/or replaceable (in some embodiments, one or more of these devices may be permanently affixed to animal cage 117). Removable and replaceable power and data components may allow for racks 405 to integrate with pumps 101 and/or medical or monitoring devices while, when removed, allowing for cleaning and, when replaced, reuse of racks 405 and the power and data communication components. Data hubs 601 may reduce workspace clutter (wired and/or wireless) and may reduce the risk of data transmission interference between various devices.

Figure 8:
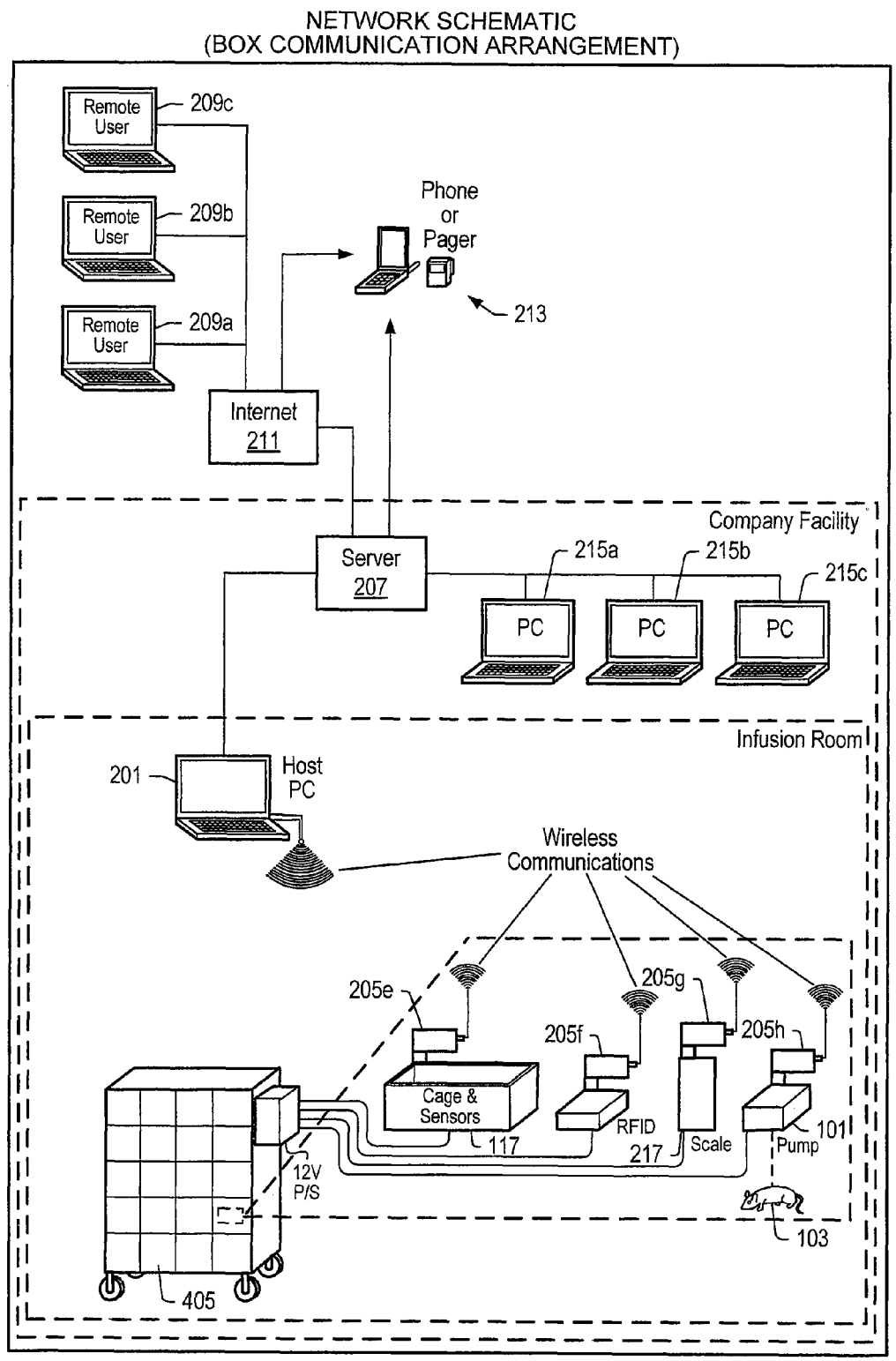
FIG. 8 illustrates a box communication arrangement with a pump and medical and monitoring devices respectively coupled to a removable piece of wireless communications hardware, according to an embodiment.

FIG. 8 illustrates an embodiment of a box communication arrangement with pump 101 and/or medical or monitoring devices respectively connected (e.g., directly connected or connected through a separate piece of hardware) to a removable piece of wireless communications hardware (e.g., box 205) allowing for wireless bi-directional communication between pump 101 and/or medical or monitoring devices on animal cages 117 and computer system 201. In some embodiments, boxes 205 (e.g., boxes 205*e*, 205*f*, 205*g*, and 205*h*) may be distributed to several devices. In some embodiments, one or more boxes 205 may be shared by multiple devices. In some embodiments, rack 405 may include multiple cages 117 with integrated DC power ports and a universal, removable power supply (other configurations are also contemplated).

Figure 11:
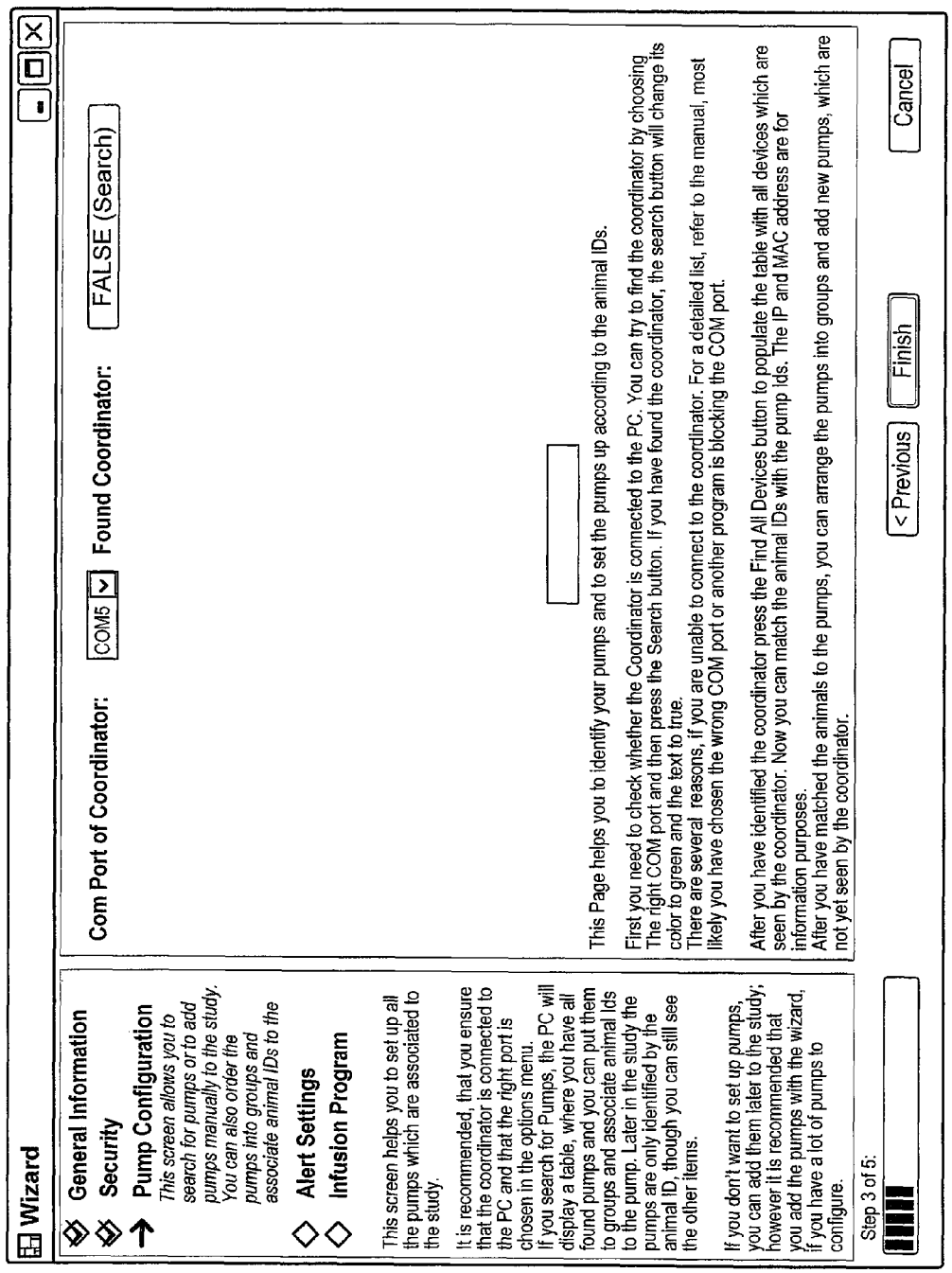
FIG. 11 illustrates a communications port set-up screen, according to an embodiment.
Figure 12:
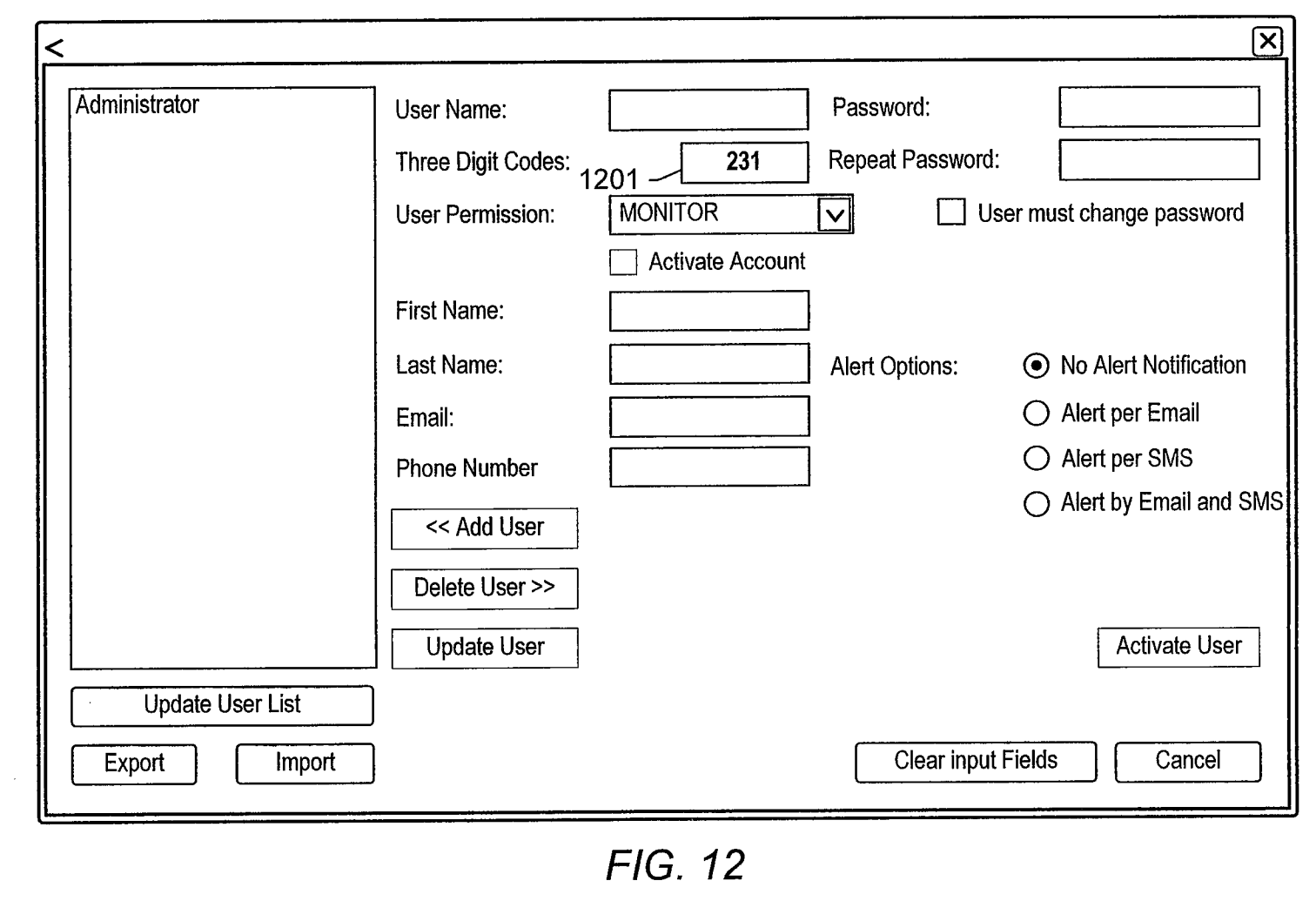
Figure 13A:
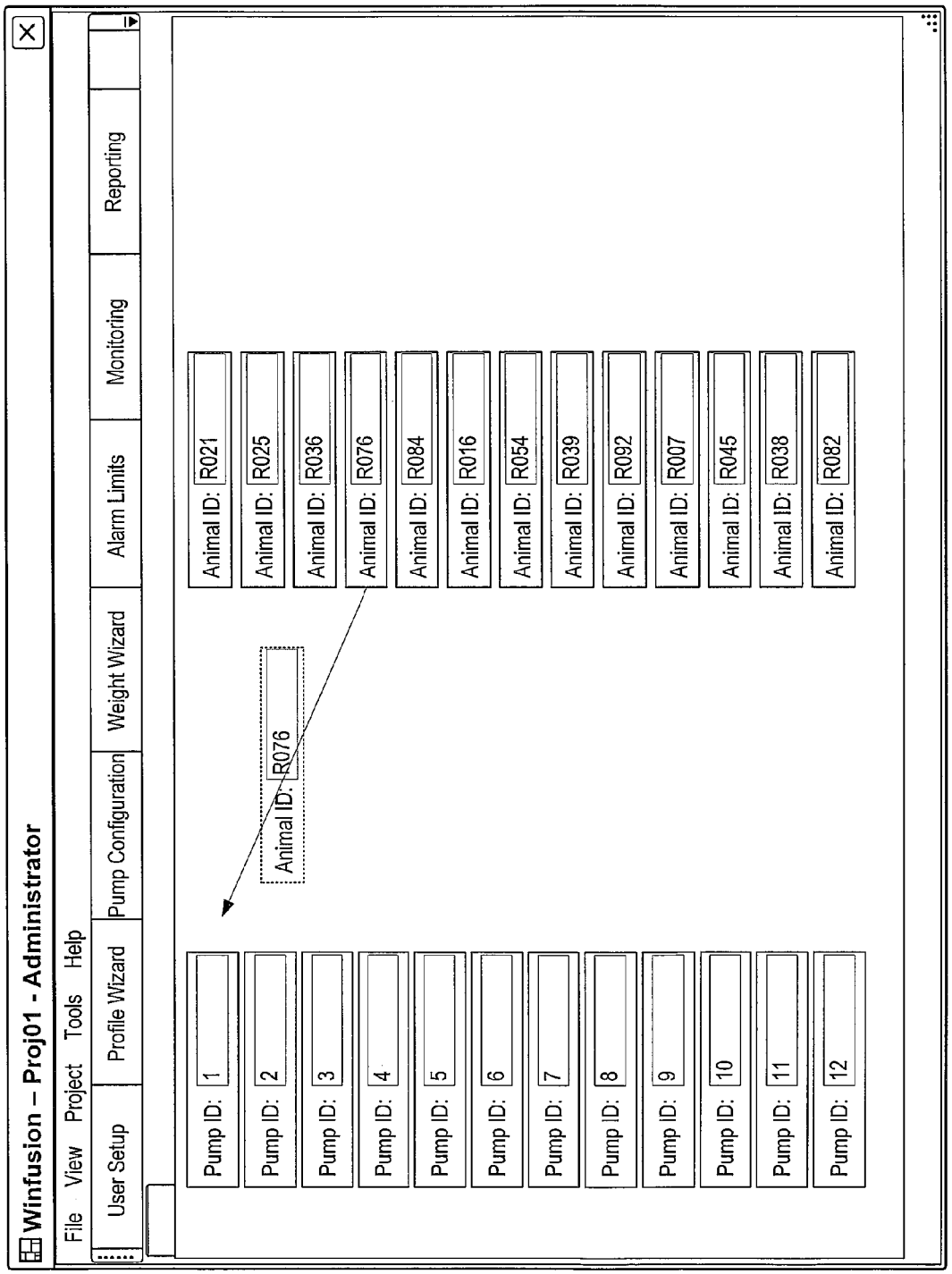
FIG. 13a illustrates a graphical user interface for pump/animal assignment, according to an embodiment.
Figure 13B:
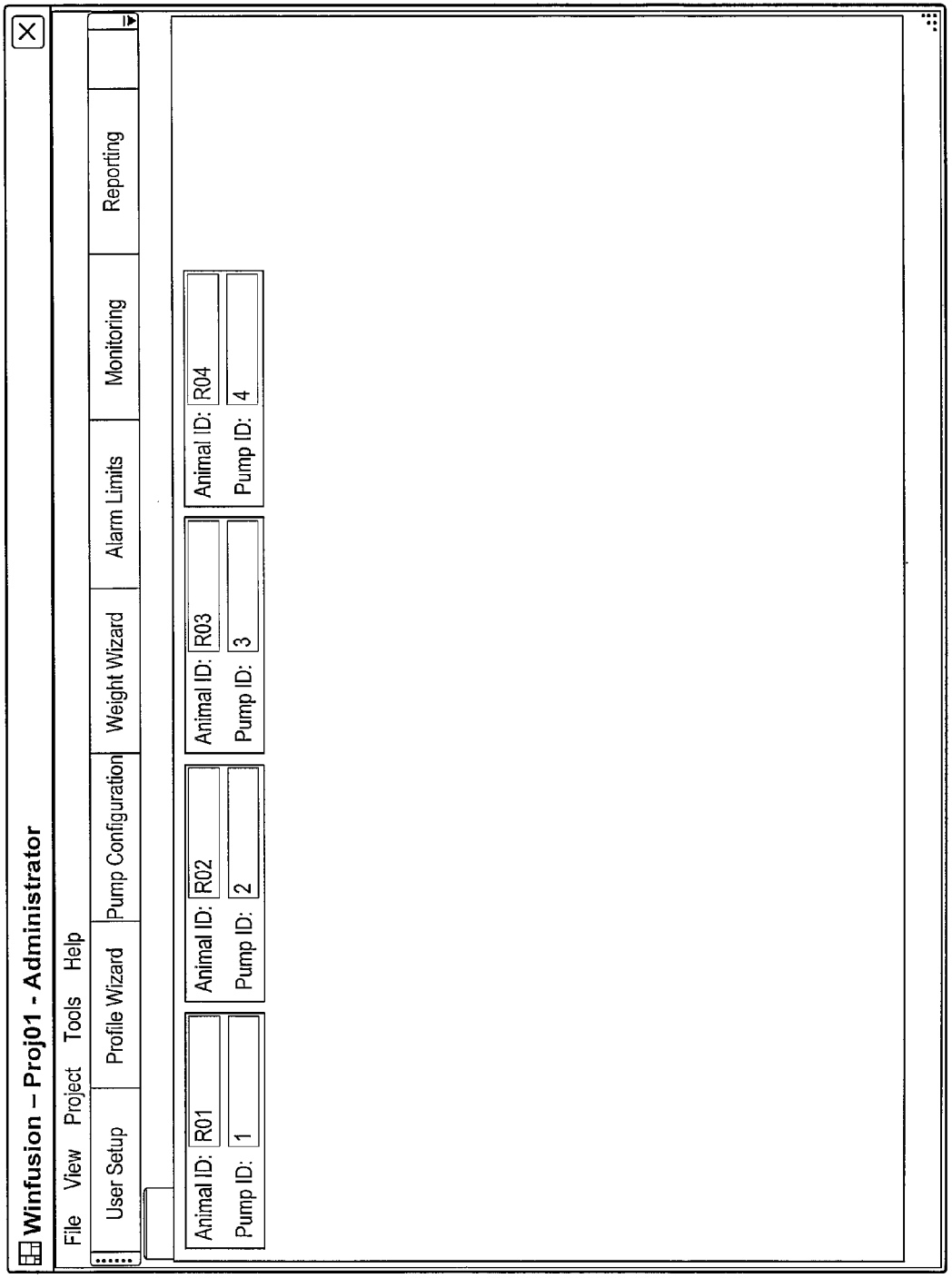
FIG. 13b illustrates graphical user interface for equipment access, according to an embodiment.
Figure 14:
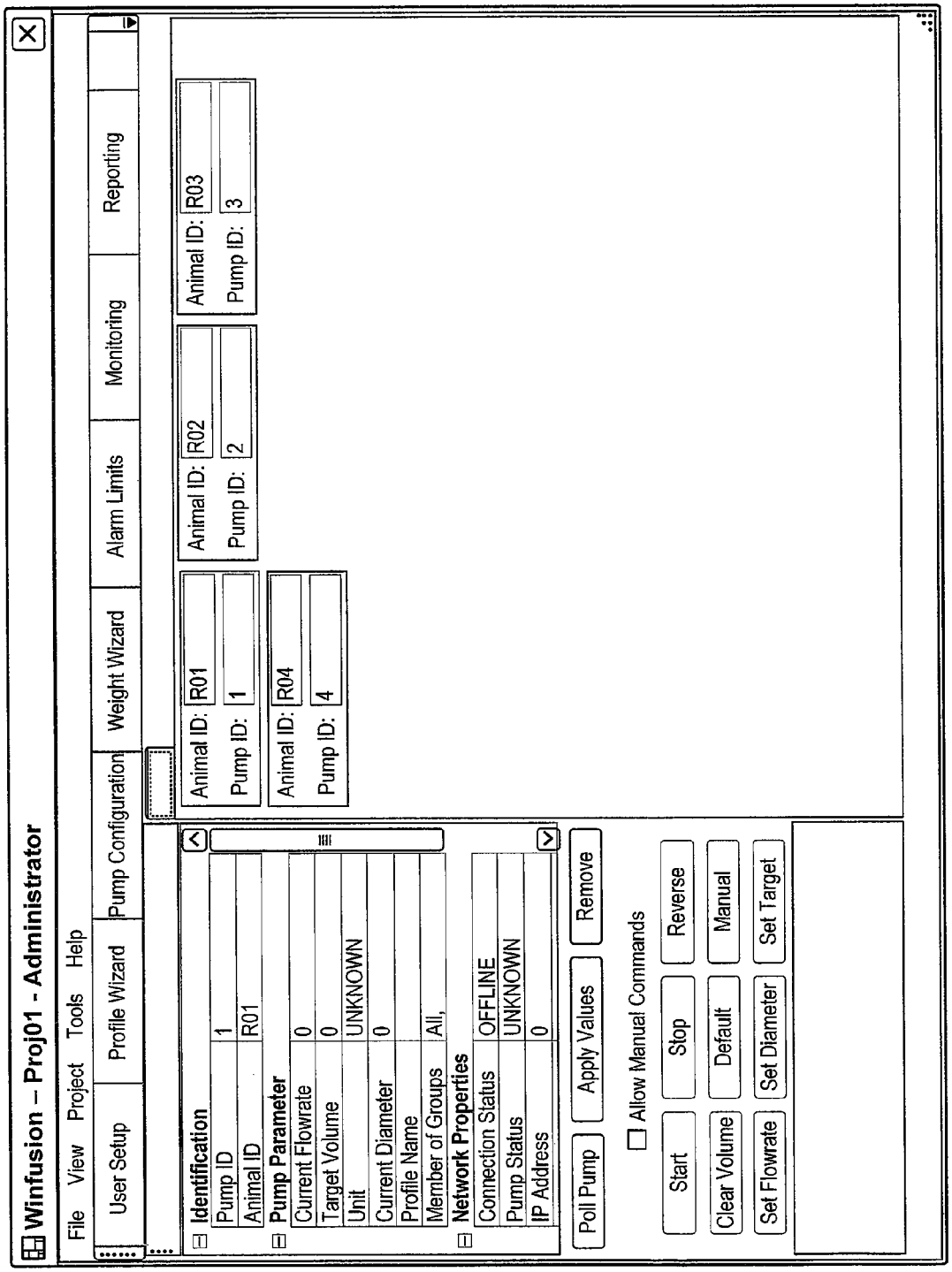
FIG. 14 illustrates a pump set-up screen, according to an embodiment.

In some embodiments, a graphical user interface (GUI) (e.g., a browser-based GUI) may be used to allow operator 401 to configure pumps 101 and/or medical or monitoring equipment (e.g., see FIGS. 9-14) through computer system 201 (or, for example, through remote computers 209*a,b,c* or 215*a,b,c*). The GUI may also allow configuration of the network which may include pumps 101, communications hardware (e.g., wireless communications hardware for networking pumps 101 to computer system 201), computer system 201 (e.g., including programming and data collection software), and a network of remote computers (e.g., computers 209*a,b,c*) linked to computer system 201 via Internet 211 and, for example, a network of remote computers (e.g., computers 215*a,b,c*) linked to computer system 201 via server 207. Other network configurations are also contemplated. As seen in FIG. 9, a GUI may be provided to assist operator 401 (e.g., a study director, technician, etc.) to set up a study. Information entered into the GUI may be used, for example, by computer system 201 to store information about the study, control the study, etc. As seen in FIG. 10, operator 401 may set up a password and specify other security parameters for the study. As seen in FIG. 11, various pumps used in the study may be set-up (e.g., communication paths may be established and/or tested between the pumps 101 and computer system 201). As seen in FIG. 12, different operators 401 may be added to a study (e.g., granted access to perform actions on pumps 101 and other equipment, document actions performed, etc). User identifiers 1201 may also be assigned to respective operators 401. As seen in FIG. 13*a*, operator 401 may assign respective pumps 101 to respective animals 103 (or vice versa). For example, computer system 201 may poll pumps 101 coupled to network 203 and pumps 101 may respond, for example, with a pump ID (see, for example, pump IDs on the left side of FIG. 13*a*). In some embodiments, computer system 201 may access respective animal IDs (e.g., from a data file, from animal RF identification chips scanned from animals 103, manually from operators 401 (e.g., reading animal tattooed IDs), etc). The animal IDs may also be listed (e.g., see the right side of FIG. 13*a*). In some embodiments, operator 401 may assign the animal IDs to their respective pumps 101. For example, the animal ID on the right side of the screen may be dragged and dropped onto the corresponding pump ID of respective pump 101 from which respective animal 103 is receiving substance 119. In some embodiments, pump IDs and/or animal IDs may be related to each other by operator 401 (e.g., by entering respective IDs in text boxes of the graphical user interface). In some embodiments, RFID readers assigned to respective cages 117 may scan RF animal ID chips and send the animal ID back to computer system 201 along with the respective pump ID for respective pump 101 providing substance 119 to cage 117 with animal 103 having the respective animal ID. Other assignment processes are also contemplated. As seen in FIGS. 13*b*-14, operator 401 may navigate the GUI to check on a status of pumps 101 and other equipment in the study, send instructions to pumps 101 and other equipment in the study, etc.

Figure 17:
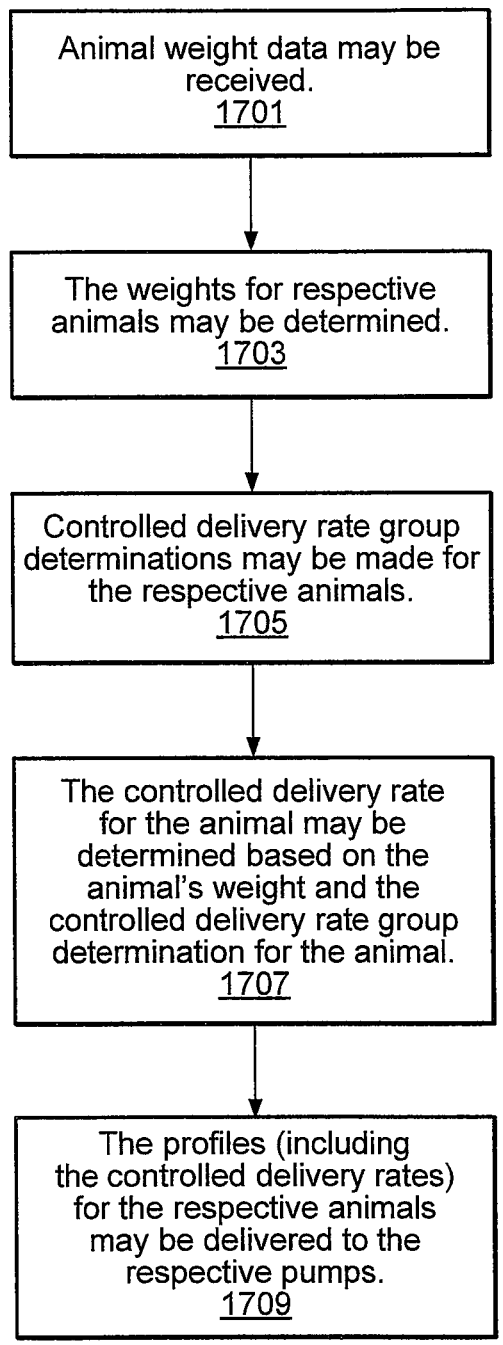
FIG. 17 illustrates a flowchart of a method for controlled delivery rate determination and global command rate distribution, according to an embodiment.

FIG. 17 illustrates a flowchart of a method for controlled delivery rate determination and global command rate distribution, according to an embodiment. It should be noted that in various embodiments of the methods described below, one or more of the elements described may be performed concurrently, in a different order than shown, or may be omitted entirely. Other additional elements may also be performed as desired.

At 1701, animal weight data may be received (e.g., by computer system 201, box 205, etc). In some embodiments, weight data may be received from weight scale 217. Weight scale 217 may be integrated into animal cage 117 (e.g., coupled to animal cage 117 or to tether 115 for passive automatic weight data collection) or may be external (e.g., animal cage 117 may be placed on top of (or hung from) weight scale 217 by operator 401). In some embodiments, multiple pumps 101 may be associated with a specific weight scale 217 (e.g., 10 pumps 101 assigned to one weight scale 217 physically located nearby). For example, operator 401 may place each animal 103 (e.g., in turn) associated with the pumps 101 on the weight scale 217 for measurement (or may place respective animal 103 from pump 101 on weight scale 217). In some embodiments, weight data from weight scale 217 may be communicated to computer system 201. For example, computer system 201 may receive weight data from weight scale 217 through data hub 601 and/or box 205 coupled to weight scale 217. As another example, weight scale 217 may be coupled to pump 101 and weight data from weight scale 217 may be sent to pump 101 (or box 205 coupled to pump 101) for communication to computer system 201. In some embodiments, the weight data may be automatically communicated to computer system 201 and stored in a database (e.g., an operator's project software database). In some embodiments, the weight data may be sent to computer system 201 when an instruction is received by weight scale 217 or pump 101 (e.g., from operator 401). As another example, in some embodiments, the weight data may be sent in response to a query from computer system 201. Other weight data sources are also contemplated. For example, animal weight data may be received from a customer database on a server, from a database in a computer hosting infusion system, etc. Computer system 201 may query a database for the weight data to be imported into computer system 201. In some embodiments, operators 401 may load the data directly into computer system 201 (e.g., by inserting a Compact Disc (CD) with the weight data, manually entering the weight data, etc). In some embodiments, new weight data may be received as new animal weights are determined. For example, animals 103 may be weighed continuously or at intervals (e.g., animal 103 may be weighed daily, weekly, monthly, etc). In some embodiments, animal weights and respective animal weights may not be determined (e.g., if the controlled delivery rates are not weight based).

At 1703, the weights for respective animals 103 may be determined. Animals 103 may be associated with specific pumps 101 and computer system 201 may associate weight data with respective pumps 101. For example, if weight scale 217 is coupled to or assigned to one respective pump 101, the weight data received from that weight scale 217 may be associated (e.g., in a database) with animal 103 at that respective pump 101. In some embodiments, (e.g., if multiple pumps 101/cages 117 are assigned to weight scale 217) identifiers (e.g., entered by operator 401 into weight scale 217, scanned by an RFID scanner when animal 103 with an embedded RFID chip containing the identifier is placed on weight scale 217, etc.) may be sent with the weight data to computer system 201 as the animals 103 (or cages 117, etc.) are weighed to associate the received weight data with the respective animal 103/pump 101. In some embodiments, identifiers may be stored in the database with the weight data to associate the weight data with respective animals 103 and/or pumps 101 (respectively assigned to animals 103). In some embodiments, identifiers may not be used. For example, weight data may be associated with respective animals 103 according to an order the weights were entered (which may correspond to a predetermined order of pumps 101 in relationship to the weight scale 217). For example, 10 pumps 101 may be assigned to a weight scale at the end of the row of pumps 101. When the animals 103/cages 117 are weighed, operator 401 may always start with the cage farthest from weight scale 217 and proceed down the line of cages 117 to the cage nearest weight scale 217 (computer system 201 may be aware of the order of cages 117 and may assign the weights to respective animals 103 according to the order the weights were received. Other weight associations are also contemplated. The animal 103 may be weighed on weight scale 217 directly or, for example, cage 117 and be weighed and the animal's weight may be derived (e.g., by subtracting a predetermined weight of the empty cage). Other weight data sources are also contemplated (e.g., the weight data may be imported from a separate software program or database, manually entered, etc).

At 1705, controlled delivery rate group determinations may be made for the respective animals 103. In some embodiments, animals 103 may be assigned to different study groups (e.g., high dose group, mid-dose group, low dose group, and control, etc). Group assignments may be downloaded to computer system 201 (e.g., from an external computer), manually entered (e.g., by operator 401), or determined according to criteria (e.g., entered by operator 401). For example, operator 401 may specify 1000 cages will be used in the study and 25% are to be assigned to a high dose group, 25% to a mid dose group, 25% to a low dose group and 25% to a control group. This criteria may also be downloaded from an external source. Computer system 201 may have access to (or may determine) which pumps 101 are currently communicatively coupled to computer system 201 (e.g., through a broadcast query and subsequent pump responses) and the pumps 101 may be initially assigned to different respective groups (e.g., computer system 201 may determine and store assignments in a database for later access). In some embodiments, respective controlled delivery rates (e.g., [dose/time]/kg×animal weight ([ml/hr]/kg×kg of animal weight)) may be associated with respective groups of animals. For example, the respective controlled delivery rates may be downloaded from an external source, manually entered by operator 401, etc. Additional study parameters may also be received and/or determined. For example, an amount of time to deliver the respective doses may also be received (e.g., downloaded from an external source, manually entered by operator 401, etc). For example, computer system 201 may receive and store an indication that the specified controlled delivery rates are to be delivered for one hour a day. Computer system 201 may also receive the total trial length (e.g., 30 days). In some embodiments, complex profiles may be received (e.g., controlled delivery rate for one hour per day for 15 days and 2 hours per day for 15 days). Other profiles are also contemplated. Computer system 201 may store controlled delivery rates, time periods, profiles, etc. to be used in determining controlled delivery rate for respective animals 103 in the study.

At 1707, the controlled delivery rate for animal 103 may be determined based, for example, on the animal's weight and the controlled delivery rate group determination (e.g., the controlled delivery rate assigned to the animal's group). For example, for a specific animal 103 in a high dose group, a predetermined controlled delivery rate of [100 ml/hr]/kg×kg of body weight may be assigned (e.g., by computer system 201 based on received data). In this example, if the weight data for the specific animal 103 indicates the specific animal 103 weighs 0.7 kg, the controlled delivery rate for a pump 101 pumping substance 119 to the specific animal 103 is [100 ml/hr]/kg*0.7 kg=70 ml/hr. Computer system 201 may also use the received time periods to determine a dose per time period of delivery. For example, study parameters may specify the high dose group should receive the specified controlled delivery rate for 1 hour a day. In the above example, computer system 201 may then prepare a profile with instructions for respective pump 101 to deliver 70 ml of substance 119 to respective animal 103 for one hour every 24 hours. Study parameters may also specify the animals 103 are to receive saline solution during the hours animals 103 are not receiving substance 119 in order that the positive saline flow reduces the risk of catheter clotting. Other controlled delivery rate calculations are also contemplated for the other groups (e.g., mid dose, low dose, etc). Other time periods may also be used (e.g., 2 hrs/day, 2 min/day, 1 hour every 3 days, etc). In some embodiments, computer system 201 may determine multiple respective profiles with instructions for respective animals in the study according to their respective weights and their respective dose groups.

At 1709, the profiles for respective animals 103 may be delivered to the respective pumps 101. In some embodiments, the profiles may include respective controlled delivery rates, relevant time periods for delivery (e.g., indicating number of hours every 24 hours for delivery and total study period), start/stop times, etc. In some embodiments, a global command may instruct computer system 201 to send the multiple profiles to their respective pumps 101 (e.g., in some embodiments, all of the pumps 101 in the study may receive their specific profile from computer system 101). In some embodiments, a subset of pumps 101 may be sent their respective profiles in response to the global command (e.g., the global command may instruct computer system 201 to send profiles to pumps 101 in the high dose group). As another example, the global command may instruct computer system 201 to send profiles to pumps 101 with animals in a certain weight group (e.g., with animals 103 having weights between 0.5 kg and 0.6 kg) or to animals of a certain gender (e.g., all male animals). Other groups are also contemplated. In some embodiments, multiple groups may be specified (e.g., profiles may be sent to the low dose group and the placebo group in response to receiving the global command). In some embodiments, multiple profiles may be pushed to their respective pumps 101 after performing a sequence of calculations (e.g., by computer system 201) to generate the multiple profiles. In some embodiments, operator 401 may indicate when to send the profiles (e.g., by pressing a button (or by some other input) on computer system 201 (e.g., to select an on screen menu item), sending a command to computer system 201 from a remote device, etc). As part of the global command, operator 401 may also specify which groups (or, for example, all of the pumps 101) to send profiles. In some embodiments, computer system 201 may deliver infusion rate commands (e.g., including controlled delivery rates based on the animals weight and determined group weight-based controlled infusion rates) to pumps 101 individually instead of in groups.

Other global commands are also contemplated. For example, a global command may instruct computer system 201 to send other instructions to multiple pumps 101 and/or medical or monitoring devices on the network. For example, the global command may cause computer system 201 to send other instructions to pumps 101 instead of or in addition to inputting commands (e.g., by operator 401) to pumps 101 on a one-by-one basis. In some embodiments, the global command may instruct computer system 201 to send inquiries to pump 101, a group of pumps 101, or all of pumps 101 in the study. For example, upon receiving an indication from operator 401, computer system 201 may request information from a group of pumps 101 (such as current amount of delivery time remaining, last calibration date, etc). In some embodiments, the global command may reduce the manpower needed to perform and send the calculations, reduce manual calculation errors, and reduce manual data input errors. In some embodiments, the global command may be used to automate scheduling to reduce scheduling errors by including start/stop times with the profiles delivered to respective pumps.

In some embodiments, the instructions for determining a controlled delivery rate may be included in box 205 (or, for example, internally to pump 101). Pumps 101 may determine their respective controlled delivery rate based on the stored instructions, the animal weight (e.g., received at pump 101 from weight scale 217), and other information (e.g., the dose/ body weight for animal 103 associated with respective pump 101, times for delivery, etc). In some embodiments, pumps 101 may perform the calculations to determine their own controlled delivery rates (e.g., computer system 201 may send a global command to pumps 101 to calculate their controlled delivery rates). In some embodiments, the calculated controlled delivery rates (and, for example, animal weight data) may be sent by pumps 101 to computer system 201 (e.g., for storage and/or validation). Other locations for controlled delivery rate determination are also contemplated.

Figure 18:
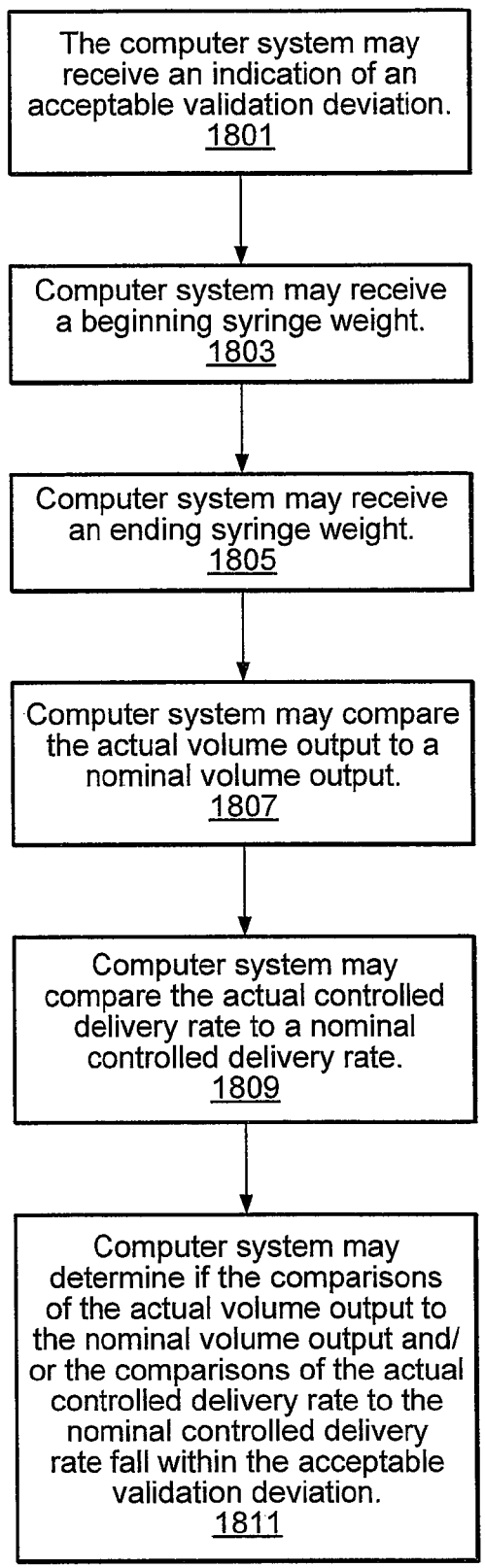
FIG. 18 illustrates a flowchart of a method for pump validation, according to an embodiment.

FIG. 18 illustrates a flowchart of a method for pump validation, according to an embodiment. It should be noted that in various embodiments of the methods described below, one or more of the elements described may be performed concurrently, in a different order than shown, or may be omitted entirely. Other additional elements may also be performed as desired.

At 1801, computer system 201 may receive an indication of an acceptable validation deviation. For example, operator 401 may indicate that an acceptable validation deviation of +/−1% of actual syringe weight difference (before and after substance delivery) compared to calculated syringe weight difference (based on pump determined substance delivery and substance density) is acceptable. In some embodiments, the acceptable validation deviation may be received from other sources (e.g., downloaded from a remote computer). Acceptable validation deviations may also be specified in other terms. For example, an acceptable validation deviation may include +/−X % of actual controlled delivery rate (e.g., determined using the difference in syringe weights, density of substance 119, and start/stop times from pump 101) compared to provided/calculated controlled delivery rate (e.g., the controlled delivery rate provided to pump 101). Other acceptable validation deviations are also contemplated. Acceptable validation deviations may be provided in non-percent indicators. For example, operator 401 may be prompted to enter an acceptable validation deviation as a difference in weight (e.g., +/−X ml) between the actual volume output and the provided/calculated volume output (e.g., X=actual volume−volume provided to pump 101 in profile instructions). Other sources of acceptable validation deviations are also contemplated. In some embodiments, a range of acceptable validation deviations may be received.

At 1803, computer system 201 may receive a beginning syringe weight. In some embodiments, operator 401 may place syringe 109 on weight scale 217 prior to delivering substance 119. For example, operator 401 may place syringe 109 for pump 101 on a shared weight scale 217 (e.g., shared with other pumps 101). In some embodiments, the weight (and, for example, a pump identifier) may be sent to computer system 201 by weight scale 217. In some embodiments, weight scale 217 may be built into pump 101 to weigh syringe 109 without syringe 109 having to be removed from pump 101 (the weights (and/or weight difference) may be sent to computer system 201 by pump 101).

In some embodiments, operator 401 may be prompted to enter a beginning syringe weight. For example, operator 401 may enter the weight into computer system 201 or into pump 101 (e.g., for delivery to computer system 201). For example, operator 401 may place syringe 109 on weight scale 217, see weight of syringe 109 (e.g., on a display of weight scale 217), and may enter the weight in, for example, pump 101 associated with animal 103 or computer system 201. Other sources of the beginning syringe weight are also contemplated. In some embodiments, weight scale 217 on, in, or proximate to animal cage 117 or pump 101 (e.g., one weight scale 217 per pump 101 or animal cage 117 or one weight scale 217 per a group of pumps 101 or animal cages 117) may communicate weights of syringe 109 to computer system 201 (e.g., through box 205 coupled to the weight scale 217). For example, weight scale 217 may determine a weight of syringe 109 prior to delivering substance 119 to animal 103.

At 1805, computer system 201 may receive an ending syringe weight. In some embodiments, weight scale 217 may determine a weight of syringe 109 after delivering substance 119 to animal 103 (e.g., operator 401 may place syringe 109 on weight scale 217 after the delivery time period or weight scale 217 may be built into pump 101). In some embodiments, operator 401 may be prompted to enter ending syringe weight. For example, operator 401 may place syringe 109 on weight scale 217, see weight of syringe 109 (e.g., on a display of weight scale 217), and may enter the weight in, for example, pump 101 associated with animal 103 or computer system 201. Other sources of the ending syringe weight are also contemplated.

At 1807, computer system 201 may compare the actual volume output (determined using the substance density and the difference in the beginning syringe weight and the ending syringe weight) to a nominal volume output (e.g., an expected volume output based on the calculated controlled delivery rate delivered to pump 101 by computer system 201 prior to delivery).

At 1809, computer system 201 may compare the actual controlled delivery rate (e.g., using substance density, difference in the beginning syringe weight and the ending syringe weight and a received actual start time and end time from pump 101) to a nominal controlled delivery rate (e.g., based on the calculated controlled delivery rate delivered to pump 101 by computer system 201). In some embodiments, computer system 201 may receive a start and stop time (or, for example, a total time of delivery) to use with the received weights to calculate the pump's actual controlled delivery rate. In some embodiments, computer system 201 may compare an actual controlled delivery rate (e.g., ((beginning syringe weight−ending syringe weight)/substance density/(stop time−start time)) to a calculated/provided delivery controlled delivery rate (e.g., calculated by computer system 201 prior to substance delivery and provided to pump 101 as the respective controlled delivery rate for respective animal 103) to determine an accuracy of pump 101. Other information may also be sent to computer system 201 (e.g., a controlled delivery rate determined locally by pump 101). Other controlled delivery rate determination calculations are also contemplated. For example, computer system 201 or pump 101 may use a displacement volume and delivery time to determine an actual controlled delivery rate. The displacement volume may be determined using dimensions of syringe 109 (e.g., radius of a cylindrical syringe) and, for example, the amount of plunger displacement (e.g., indicated by a sensor on pump 101) (where displaced volume may equal the amount of displacement * internal area (e.g., $\pi * radius^2$). The actual controlled delivery rate may be represented by the displaced volume over time of displacement (e.g., as determined by start and stop times). In some embodiments, information such as the dimensions of syringe 109 may be received by computer system 201 (e.g., from pump 101 detecting a diameter of syringe 109, operator 401, or other external source).

At 1811, computer system 201 may determine if the comparisons of the actual volume output to the nominal volume output and/or the comparisons of the actual controlled delivery rate to the nominal controlled delivery rate fall within the acceptable validation deviation (e.g., as determined/received at 1801). For example, the actual controlled delivery rate may be compared to the nominal controlled delivery rate (e.g., the controlled delivery rate provided to pump 101 by computer system 201 for the corresponding time period (or, for example, the controlled delivery rate calculated by pump 101 for the corresponding time period)). In some embodiments, comparison may include subtracting the actual volume output from the nominal volume output (or vice versa) and comparing the difference to an acceptable validation deviation (which may include a range of acceptable differences between the actual volume output and the nominal volume output). In some embodiments, comparison may include subtracting the actual controlled delivery rate from the nominal controlled delivery rate (or vice versa) and comparing the difference to an acceptable validation deviation (which may include a range of acceptable differences between the actual controlled delivery rate and the nominal controlled delivery rate). Other statistical comparisons are also contemplated. As another example, the weight (or, for example, volume) of actual substance 119 delivered (collected infusate) may be plotted versus time along with a plot of the weight (or, for example, volume) of substance 119 that would be delivered versus time according to the nominal controlled delivery rate. In some embodiments, operator 401 may review the plots for semi-automatic validation. In some embodiments, accuracy may be provided as a +/−X % accuracy (e.g., representative of the difference between the actual controlled delivery rate and the nominal controlled delivery rate). In some embodiments, the validation may be fully automatic (e.g., computer system 201 may compare statistics of the validation against acceptable validation ranges). In some embodiments, indications of the success or failure of validation may be presented to operator 401. For example, accuracies falling out of the acceptable ranges may be reported (e.g., to operator 401) as pump 101 failing validation. Validation may be performed prior to (e.g., with a dummy substance 119), during (e.g., with the actual substance 119 delivered to animal 103), and/or after a lab animal infusion study. In some embodiments, each pump 101 may be validated or a sampling of pumps 101 may be validated. In some embodiments, if pump 101 fails validation, pump 101 may not be used until successfully validated. In some embodiments, automated validation may reduce the manpower needed to perform and send the calculations, reduce manual calculation errors, and reduce manual data input errors. In some embodiments, the validations may be performed according to an automated schedule to reduce scheduling errors. In addition, automated validations may allow for an increased validation frequency (e.g., pumps 101 may be validated before a study, one or more times during the study, and after the study).

In some embodiments, pumps 101 may be calibrated (e.g., on a regular basis such as once a year). Calibration may include testing controlled delivery rate accuracy over a period of time (e.g., comparing actual pump controlled delivery rate to instructed pump controlled delivery rate). Calibration may further include comprehensive periodic checks to confirm proper pump functioning (e.g., several aspects of pump 101 may be checked with sensors, etc. to insure proper functioning). In some embodiments, information related to the next calibration may be stored, for example, on computer system 201, pump 101, box 205, etc. Calibration information may include a date pump 101 was last calibrated, a next date pump 101 should be calibrated by, etc. Calibration information may be stored, for example, in firmware in pump 101 (or, for example, coupled to pump 101 (such as in memory 305)). Calibration information may also be included on an outside of pump 101 (e.g., written on a pump label). Computer system 201 (or executable instructions on box 205, etc.) may check the calibration information (e.g., prior to the beginning of a study) and may indicate (e.g., to operator 401) pumps 101 that have surpassed their calibration interval (or will surpass their calibration interval during the study). For example, if the calibration dates are stored at pumps 101, computer system 201 may poll pumps 101 in the network for their calibration dates to determine if any of pumps 101 are outside of their calibration period or will be outside the calibration period at any time during the next study. In some embodiments, computer system 201 (or, for example, box 205) may prevent use of pump 101 until pump 101 is calibrated and the information stored for pump 101 indicates that the calibration is current. In some embodiments, a calibration database may include pump identifiers and respective calibration dates for pumps 101 (e.g., the calibration dates may not be stored in the pumps 101). In some embodiments, operators 401 may read calibration information on pump 101 (e.g., on an outer label) and may enter the calibration information into an interface on pump 101 and/or computer system 201 to be stored. Computer system 201 may poll pumps 101 to determine pump identifiers (indicating which pumps 101 are currently coupled to the network) and compare this list of pumps 101 to the calibration database to determine if the current pumps 101 have current calibration dates. Computer system 201 may alert operator 401 as to which pumps 101 have calibration problems to allow operator 401 to replace and/or calibrate the problem pumps 101. In some embodiments, computer system 201 (or, for example, box 205) may calibrate pump 101 (e.g., using techniques described above). Other calibration techniques are also contemplated. Automating the calibration check may save time, assure compliance with documentation requirements, and reduce the risk of human error.

Figure 19:
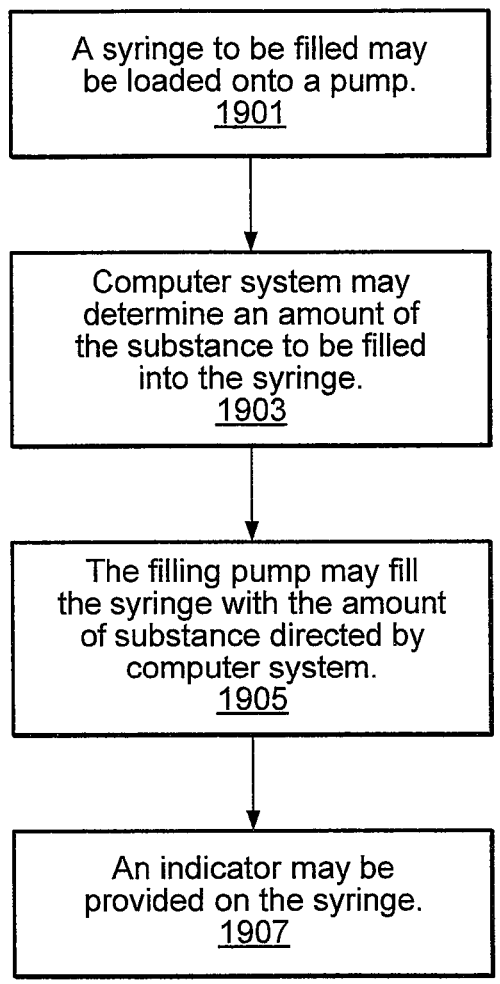
FIG. 19 illustrates a flowchart of a method for automated syringe filling, according to an embodiment.

FIG. 19 illustrates a flowchart of a method for automated syringe filling, according to an embodiment. It should be noted that in various embodiments of the methods described below, one or more of the elements described may be performed concurrently, in a different order than shown, or may be omitted entirely. Other additional elements may also be performed as desired.

At 1901, syringe 109 to be filled may be loaded onto pump 101. For example, computer system 201 may instruct operator 401 to load syringe 109 onto a filling pump (which may be a pump 101). In some embodiments, computer system 201 may instruct operator 401 to attach a vat holding substance 119 to be loaded into syringe 109 to pump 101 (or the vat may already be attached to syringe 109 on pump 101). In some embodiments, pumps 101 at animal cages 117 may fill syringe 109 (e.g., operator 401 may carry the vessel from pump 101 to pump 101 and the filling instructions may be sent by computer system 201 to respective pump 101). For example, pump 101 may be a bi-directional pump 101 capable of pulling the appropriate fluid volume into syringe 109 (e.g., by pulling plunger of syringe 109 to fill syringe 109). In some embodiments, pump 101 for filling syringe 109 may be located next to respective animal cage 117 or may be a separate pump 101 (e.g., communicatively coupled to computer system 201 but not necessarily at animal cage 117).

At 1903, computer system 201 may determine an amount of substance 119 to be filled into syringe 109. For example, computer system 201 may determine an amount of substance 119 needed for a next round of delivery for a respective animal 103 (e.g., based on a controlled delivery rate assigned to animal 103). In some embodiments, computer system 201 may determine an amount of substance 119 to be delivered by pump 101 during a next phase of the study and the amount may be communicated to pump 101.

At 1905, filling pump 101 may fill syringe 109 with the amount of substance 119 directed by computer system 201. For example, pump 101 may pull the syringe plunger backward to aspirate fluid (e.g., substance 119) from a vessel into syringe 109 until the directed amount is in syringe 109. In some embodiments, the filling pump 101 may operate in a reverse direction of pumps 101 delivering substance 119 to animal 103 (e.g., at the animal cages 117). Pump 101 may aspirate an appropriate volume of substance 119 on an animal-by-animal (pump-by-pump) basis (e.g., for different syringes 109). In some embodiments, operator 401 may instruct pump 101 (e.g., at animal cage 117) to enter a filling mode and pump 101 may receive data from computer system 201 for the proper fill amount. In some embodiments, pump 101 may be controlled by computer system 201 (or, for example, box 205 coupled to pump 101) to load syringe 109 with a predetermined amount of substance 119. Pump 101 and/or computer system 201 may also specify to operator 401 what type of substance 119 to load into syringe 109 (and operator 401 may attach the appropriate vat of substance 119). In some embodiments, operator 401 may receive an indicator such as "Vat A" instead of or in addition to the specific type of substance 119 to load into syringe 109 (e.g., in a blind study). In some embodiments, syringe 109 may be loaded several times a day.

At 1907, an indicator may be provided on syringe 109. For example, operator 401 may write the animal identification (ID) (e.g., of the respective animal to receive the substance) and sequence of use data on syringe 109. As another example, an attached printhead may apply the data onto syringe 109 (e.g., automatically and/or by operator 401) (which may be printed directly on the syringe 109 or on a label to be coupled to the syringe 109). In some embodiments, operator 401 may apply a label generated by an attached label printer. In some embodiments, a printer (e.g., coupled to computer system 201, pump 101, etc.) may print a label for syringe 109 (e.g., with a pump identifier, the substance type, amount, animal identifier, etc.) Other information may also be printed onto the label. The label may be attached to syringe 109 (e.g., by operator 401). In some embodiments, a separate pump 101 may be used to fill syringes 109 (e.g., at a dedicated filling station (which may also have a printer)). Other filling techniques are also contemplated. Automating filling the syringe may decrease manpower needed to fill the syringe, reduce manual calculation errors and reduce manual data input errors.

In some embodiments, computer system 201 may display and/or print out a list (e.g., list 1505 in FIG. 15*b*) of dosages for future syringes 109. For example, computer system 201 may determine a dosage amount needed for multiple syringes 109 based on the respective animal weights, dosage ratios, etc. The dosage (e.g., a substance volume) for each syringe 109 may be displayed and/or printed with an identifier for pump ID, animal ID 103, dosage, approximate time/day for next syringe change, syringe type (e.g., syringe volume), etc. The displayed or printed list 1505 may allow operator 401 to pre-load syringes 109 in advance (e.g., without performing additional calculations). In some embodiments, animals 103 may be reweighed weekly (or other time interval) and the future syringes 109 for a week may be displayed (beyond a week, computer system 201 may need a new weight for animal 103 and therefore, may not be able to provide a listing past the current week). Other weigh in times (e.g., continuous, once a day, once a month, etc.) are also contemplated. The future syringe print outs may reduce manpower needed to perform the calculations, reduce manual calculation errors, and reduce manual data input errors.

In some embodiments, pump 101 may measure a size of syringe 109 (e.g., may detect a diameter of syringe 109). Pumps 101 may include a mechanism for determining a diameter of a loaded syringe 109 (e.g., a lever arm coupled to a gear to measure the diameter of syringe 109). In the lever arm example, the gear may detect a displacement of the lever arm when syringe 109 is placed between the lever arm and pump 101. Other diameter detections are also contemplated. A study may use a syringe of saline solution in an intermittent infusion profile (or a KVO (Keep Vein Open) solution to prevent catheter clotting) and a different sized syringe for a test article (TA) solution (e.g., the new chemical entity to be tested). Syringe 109 with the KVO solution may have a larger diameter than syringe 109 for the test solution. For example, the KVO solution syringe may be a 20 cubic centimeter (cc) syringe used to deliver saline solution to animal 103 for 23 hours and the test solution syringe may be a 5 cc syringe used to deliver a test solution to animal 103 for one hour. Other sizes and times are also contemplated. In some embodiments, pump 101 may detect the size (e.g., diameter and/or length) of syringe 109 in pump 101 and, if syringe 109 size does not correspond to syringe 109 that pump 101 is assigned to be pumping (e.g., as noted by instructions from computer system 201 stored, for example, in the box memory), pump 101 may give operator 401 an indicator, sound an alarm, and/or not pump syringe 109. Pump 101 may reduce human loading error to insure compliance with the provided infusion profile. In some embodiments, operator 401 may input information about syringe 109 (e.g., type of syringe, brand of syringe, size of syringe, syringe identifier, etc.) into pump 101 and/or computer system 201. The information may be stored and/or used to verify that the correct syringe 109 has been loaded.

Figure 20:
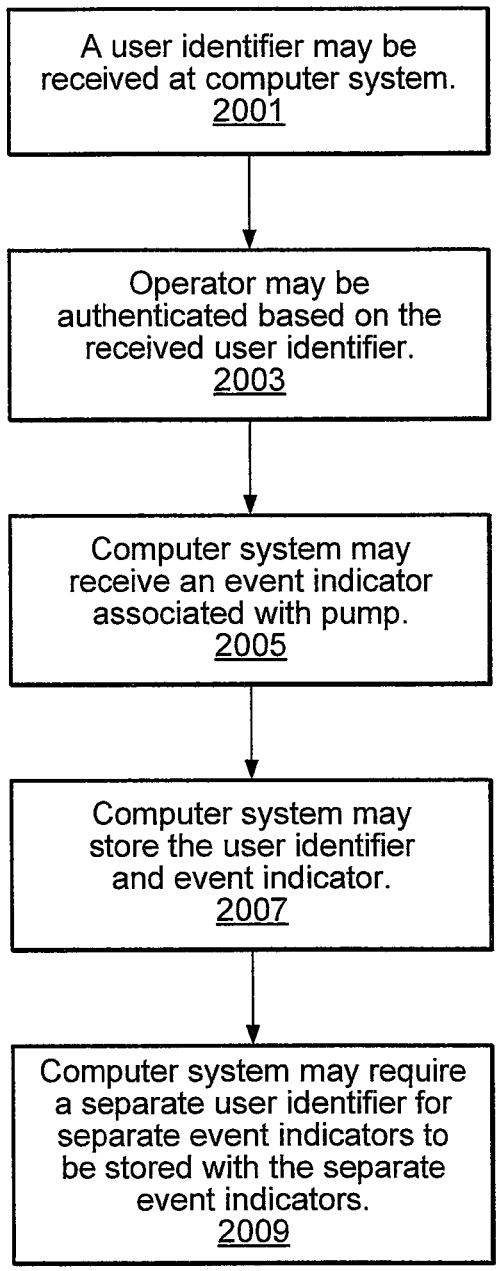
FIG. 20 illustrates a flowchart of an embodiment for study documentation.

FIG. 20 illustrates a flowchart of an embodiment for study documentation. Computer system 201 may communicate with pumps 101 and/or other medical or monitoring devices involved in the study to document events occurring in the study (e.g., start times, stop times, alarms, how alarms were cleared, animal weights, amount of feed/water consumed, etc). These events may also be stored with respective user identifiers 1201 to identify operators 401 associated with the events (e.g., to identify operator 401 who cleared an alarm). The documentation may be used to support the validity of the study. It should be noted that in various embodiments of the methods described below, one or more of the elements described may be performed concurrently, in a different order than shown, or may be omitted entirely. Other additional elements may also be performed as desired.

At 2001, user identifier 1201 may be received at computer system 201. In some embodiments, operator 401 may enter user identifier 1201 (e.g., an identifier such as a PIN code or, for example, a pre-assigned (by computer system 201) alpha numeric user code unique to operator 401) into pump 101 and/or medical or monitoring device. Other user identifiers 1201 are also contemplated (e.g., operator 401 may enter their name as user identifier 1201, scan a bar code (e.g., on the operator's uniform), swipe a magnetic card with user identifier 1201, biometric scan (e.g., scanning an user's thumbprint or retina), Radio Frequency Identification (e.g., transmitted from a PDA, etc)). User identifier 1201 may be sent to computer system 201 for storage relative to the actions performed by (or other documentation submitted by) operator 401. For example, in responding to an alarm, operator 401 may enter user identifier 1201 (e.g., into the pump interface or into computer system 201) assigned to that operator 401 prior to taking action to correct the alarm. The alarm may be indicated on computer system 201 and/or a communication (such as an email, short message service (SMS), etc.) may be sent to operator 401. The communication may include a pump identifier and an alarm type indicator (e.g., indicating why the alarm sounded). For example, if a pressure transducer on pump 101 detects an occlusion in the delivery tube, pump 101 may indicate an alarm and send a communication.

At 2003, operator 401 may be authenticated based on the received user identifier 1201. In some embodiments, user identifier 1201 may be used by pump 101 (or, for example, computer system 201, etc.) to authenticate operator 401 prior to allowing operator 401 to take action on pump 101. User identifier 1201 may thus act as user stamp/e-signature for the actions taken by operator 401. In some embodiments, operator 401 may be authenticated prior to taking action on other devices (e.g., computer system 201, medical devices, monitoring devices, animal cage 117, etc). In some embodiments, authentication may include comparing the received user identifier 1201 to user identifiers 1201 stored in an authentication database. Other authentication is also contemplated. In some embodiments, user identifiers 1201 may be changed for each study (e.g., by a study administrator who may set up which operators 401 are authorized to interact with the study equipment).

Figure 16:
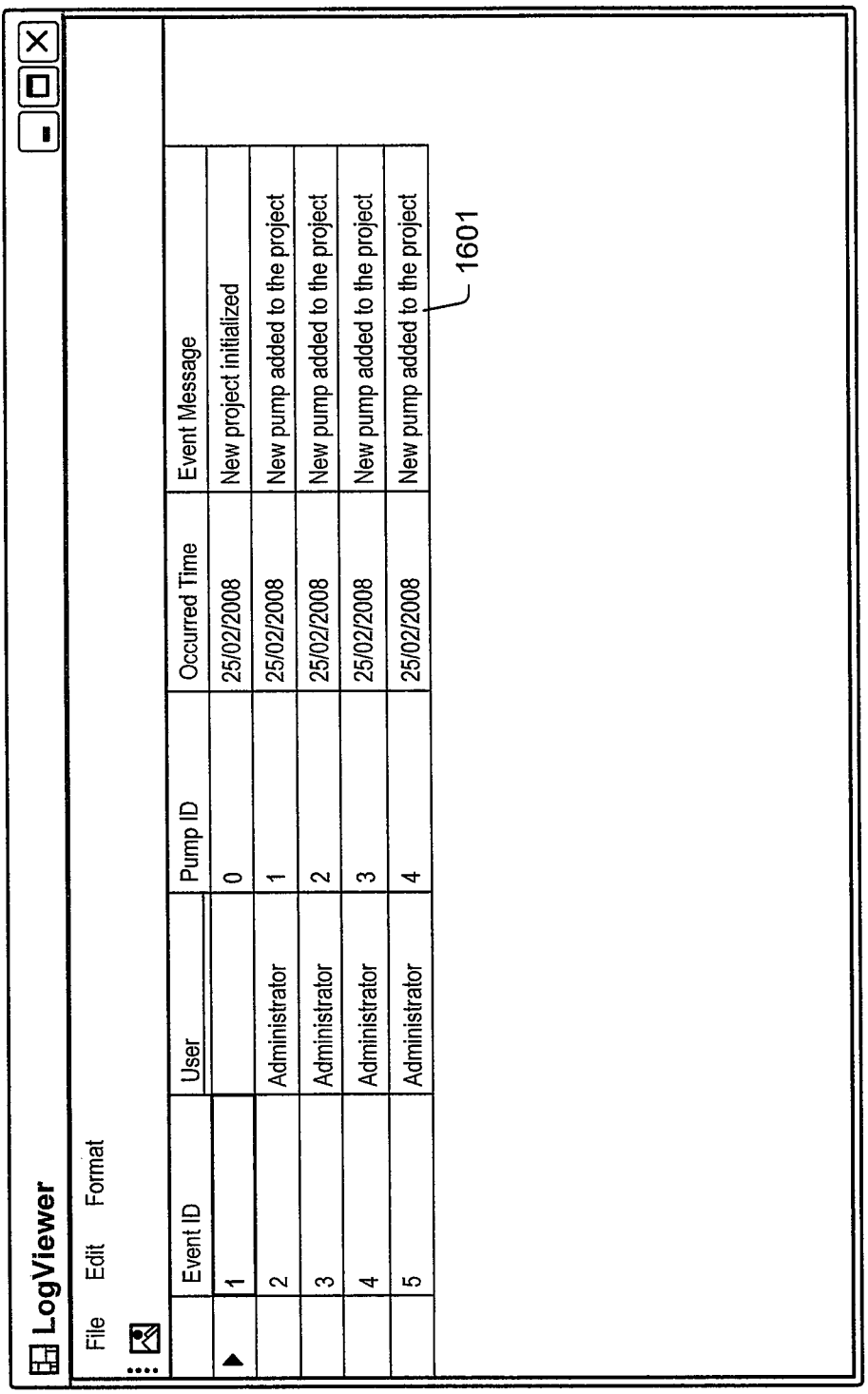
FIG. 16 illustrates an electronic log, according to an embodiment.

At 2005, computer system 201 may receive a documentation indicator associated with pump 101 (or other equipment). For example, documentation indicators (e.g., see documentation indicator 1601 in FIG. 16) may correspond to events (such as starting pump 101, responding to an alarm, stopping pump 101, etc.) and actions taken by operators 401 in response to the events. Documentation indicators 1601 may also correspond to information related to general and/or specific observations by operator 401 (e.g., animal 103 is sick) which may or may not be event specific. Documentation indicators 1601 may include a cause of an alarm. Alarms (e.g., as discussed above) may occur when equipment (e.g., pump 101) or other variables (e.g., health conditions of animal 103) in the study encounter a problem. For example, pump 101 may encounter a problem such as occlusion in delivery tube 105, low battery, no power, empty syringe, etc. When problems occur, an alarm may sound (or in some way be indicated to operator 401). Actions taken to clear an alarm may be entered (e.g., by operator 401 into a graphical interface on pump 101 or computer system 201) and a corresponding documentation indicator 1601 may be assigned. In some embodiments, operator 401 may be presented with menu (e.g., a drop down menu) and other options at computer system 201 and/or pump 101 (operator may have flexibility to document the event and/or enter other information (e.g., observations and/or non-event related information) at pump 101 or computer system 201). The menu may be specific to the type of alarm encountered. For example, if an alarm is triggered because of a kinked delivery tube, the alarm menu provided to operator 401 may include options for how the kinked delivery tube was fixed (e.g., "1: Tube unkinked"; "2: Tube replaced"; "3: Other"). In some embodiments, pump 101 may determine what caused the alarm, the actions taken by operator 401 to fix the alarm, etc. and may transmit appropriate documentation indicators 1601 to computer system 201. In some embodiments, operators 401 may enter documentation indicators 1601 indicative of what caused the alarm, the actions taken to clear the alarm, etc. into a pump interface (and/or computer system interface). Other interfaces are also contemplated (e.g., operators 401 may enter documentation indicators into a PDA which may transmit the documentation indicators 1601 to computer system 201 and/or pump 101 (e.g., to be transmitted to computer system 201)). Documentation indicators 1601 may also be stored relative to events not corresponding to an operator's actions (e.g., documentation indicator 1601 may be stored to indicate the occurrence of the alarm). Documentation indicators 1601 may be textual descriptions (e.g., "Alarm cleared by refilling syringe"). Documentation indicators 1601 may also be numerical or alpha-numerical (e.g., numbers or alpha numeric entries linked to textual description, for example, through a look-up table). Other documentation indicators 1601 are also contemplated. In some embodiments, operators 401 may define menus and menu selections for receiving documentation indicators. For example, operators 401 may define a menu for a specific type of alarm and the menu may be provided to pump 101 for presentation the next time that alarm is triggered. Operator 401 may respond to the alarm by entering appropriate menu selections and the information may be stored in computer system 201 as documentation indicators (e.g., along with the respective user identifiers 1201).

At 2007, computer system 201 may store user identifier 1201 and documentation indicator 1601. In some embodiments, computer system 201 may store corresponding documentation indicators 1601 for the operator's actions. Operator 401 may respond to the alarm and indicate on pump 101 (e.g., using a pump keypad and menu options presented on the pump display) the cause of the problem and/or how the problem was fixed. Information about the alarm, the technician identification (e.g., user identifier 1201), how the alarm was fixed, etc. may be entered into computer system 201 by operator 401 or may be entered into pump 101 and relayed to computer system 201 to be stored (e.g., in an electronic log) (see, for example, FIG. 16). Computer system 201 may store user identifiers 1201 with the corresponding documentation indicators 1601 (and, for example, a pump identifier or other device identifier).

At 2009, computer system 201 (and/or pump 101 or other equipment) may require a separate user identifier 1201 for separate documentation indicators 1601 to be stored with the separate documentation indicators 1601. In some embodiments, operator 401 may enter their user identifier 1201 prior to each action operator 401 takes on pump 101 (or in relationship to animal cage 117, medical, and/or monitoring device). In some embodiments, operator 401 may be required to enter user identifier 1201 prior to any intervention with pump 101 (or other equipment). For example, if user identifier 1201 for operator 401 is "231" and operator 401 starts and stops pump 101, operator 401 may be required to enter "231" prior to pressing a button to start pump 101 and enter "231" again prior to stopping pump 101. Computer system 201 may log documentation indicators 1601 with user identifiers 1201 (e.g., "231 start pump; 231 stop pump"). In some embodiments, computer system 201 may store a time and/or date with documentation indicators 1601. In some embodiments, computer system 201 may prompt operator 401 for additional documentation at computer system 201. For example, in clearing an alarm, operator 401 may indicate at pump 101 "other" for how alarm was cleared (e.g., using menu options provided at pump 101). Computer system 201 may then blink a screen of computer system 201, provide an alert indicator, or in some other fashion request additional description from the operator 401 as to how the pump alarm was cleared (or for other prior pump or equipment interactions). Operator 401 may enter one or more phrases, sentences, etc. in a text box that may be saved with log information for the respective pump 101. Other documentation may also be required of operator 401 (e.g., documentation may be requested for why pump 101 was stopped, why animal 103 was removed from animal cage 117, etc). In some embodiments, pump 101 may require operator 401 to enter information about the alarm (e.g., cause of problem, how the problem was fixed, etc.) prior to allowing operator 401 to continue pump operations (e.g., restart pump 101). This may force documentation of the alarm and the solution. In some embodiments, operator 401 may select "Other" in the menu options of the alarm. Operator 401 may then be prompted (e.g., at computer system 201) to enter additional information (e.g., a written statement of the problem solution) at computer system 201. In some embodiments, operator 401 may be required to enter the additional documentation before the pump 101 will be allowed to resume. In some embodiments, computer system 201 may prevent operator's future access to computer system 201 or pump 101 until the required documentation is entered. This may improve documentation by reducing human error (intentional and inadvertent) and enforcing compliance with protocols for documentation including documentation requirements.

Figure 15A:
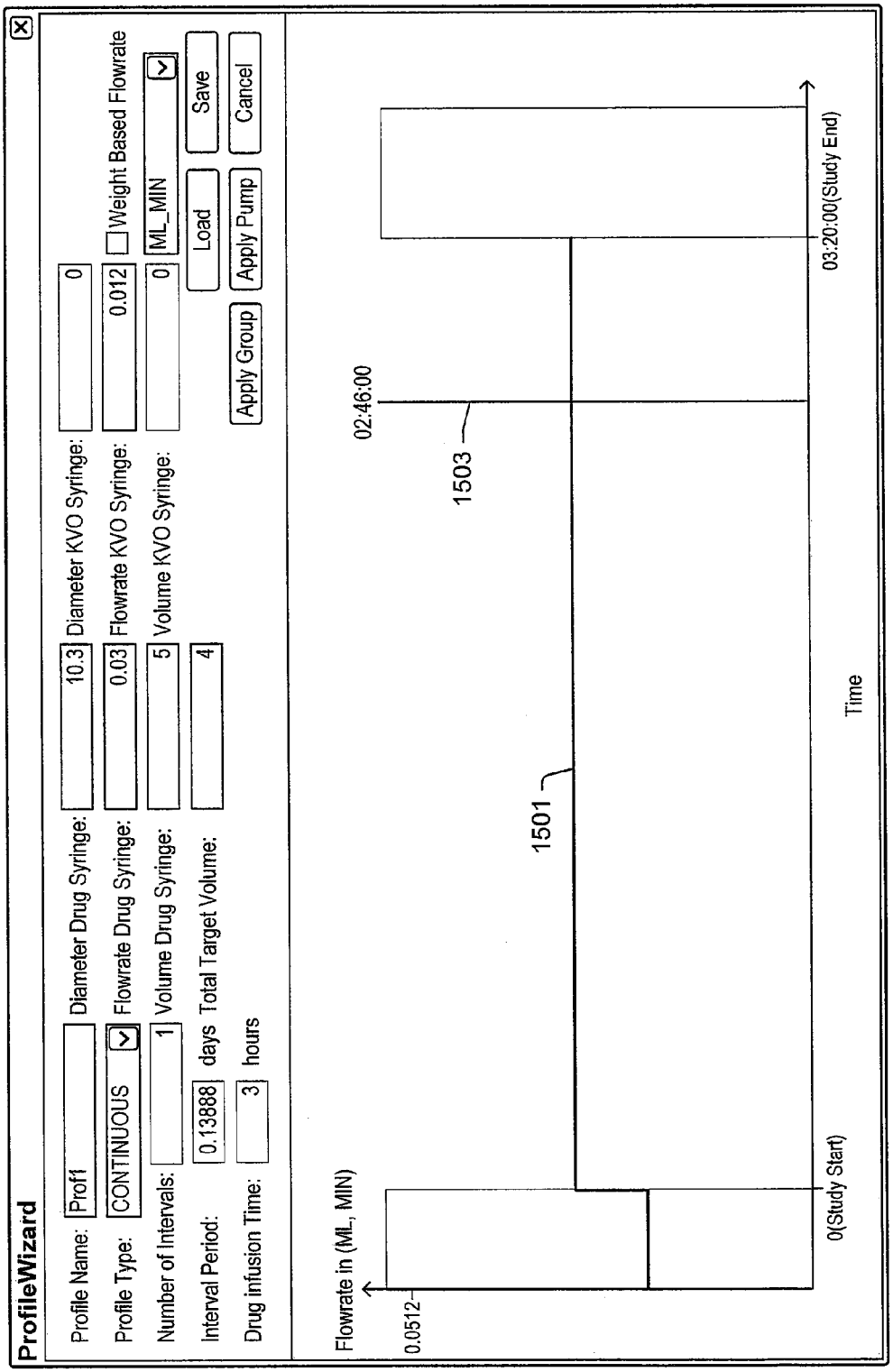
FIG. 15a illustrates a graphical profile for a substance delivery, according to an embodiment.

In some embodiments, a graphical profile of a substance delivery for a respective pump 101 may be displayed by computer system 201. For example, as seen in FIG. 15, the amount of the substance delivered (Y axis) over time (X axis) may be plotted as graphical profile line 1501. The Y axis may also be substance volume/body weight and the graphical profile may represent substance volume per weight per time unit. The graphical profile may make it easier for operator 401 to see when the syringe changes occur, what types of syringes are being exchanged (e.g., size of syringes being exchanged), etc. The profile may present a preview (e.g., which may be printed out) for one or more pumps for the study. The graphical profile may assist operator 401 in confirming proper infusion profile input and better visualize a sequence of future pump activities.

In some embodiments, indicator 1503 may be displayed on the graphical profile to indicate a current status of the substance delivery (e.g., where in the profile the current pump 101 is in the study (e.g., see line 1503)). Line 1503 may be in a different color (e.g., red) than graphical profile line 1501. Other graphical indicators 1503 are also contemplated (e.g., asterisk, arrow, etc). In some embodiments, by viewing indicator 1503, operator 401 may be able to graphically determine a current controlled delivery rate and substance type being delivered by the selected pump 101 (operator 401 may also select other respective pumps 101 to view their respective profiles). In some embodiments, indicator 1503 may assist operator 401 in determining what point in the infusion profile pump 101 is current operating. For example, operator 401, upon viewing indicator 1503, may determine whether pump 101 is at a point in the infusion profile for a KVO syringe or a TA syringe.

Figure 21:
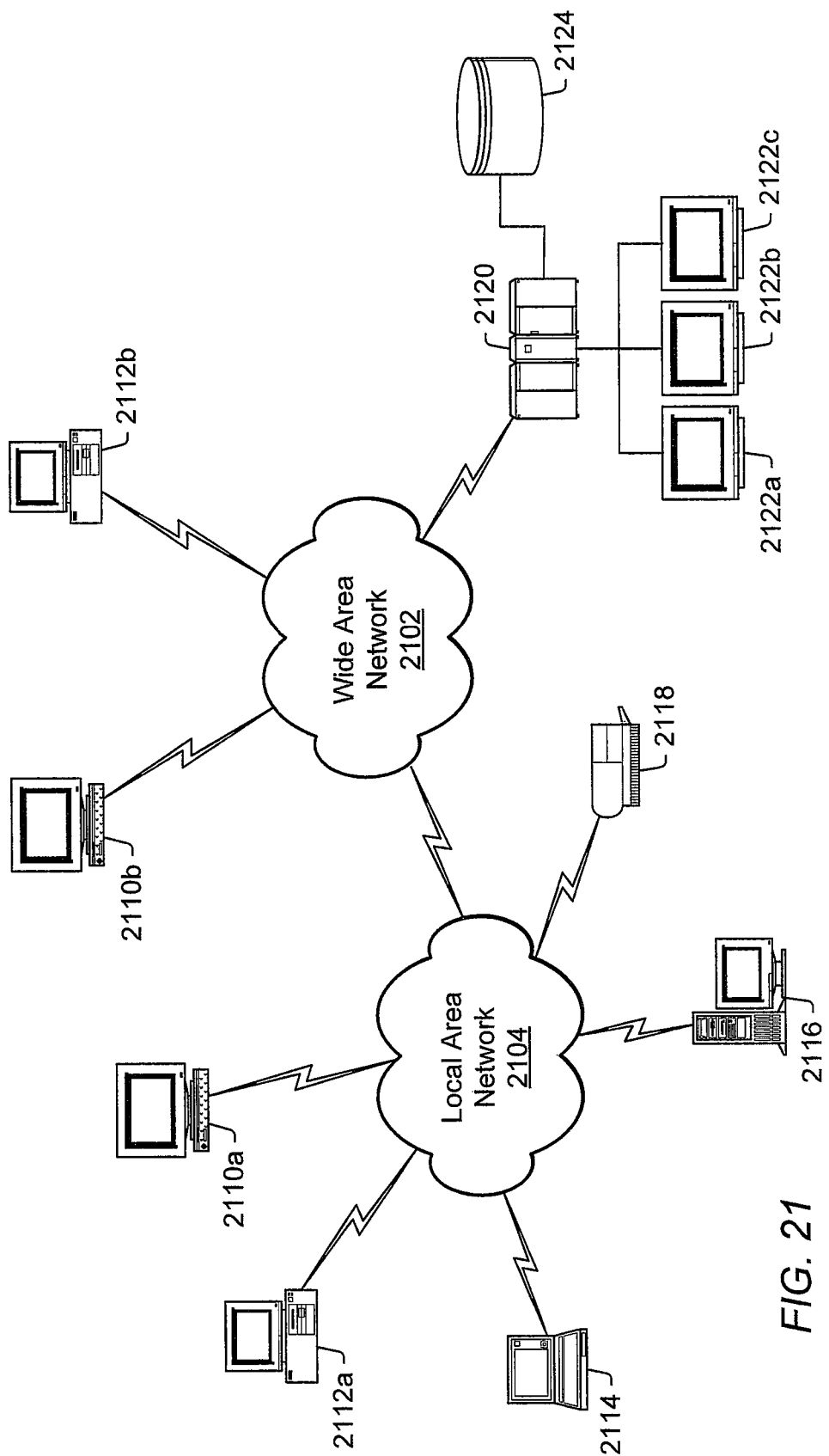
FIG. 21 illustrates an embodiment of a wide area network (WAN) and a local area network (LAN).

FIG. 21 illustrates an embodiment of a WAN 2102 and a LAN 2104. WAN 2102 may be a network that spans a relatively large geographical area. Internet 211 is an example of a WAN 2102. WAN 2102 typically includes a plurality of computer systems that may be interconnected through one or more networks. Although one particular configuration is shown in FIG. 21, WAN 2102 may include a variety of heterogeneous computer systems and networks that may be interconnected in a variety of ways and that may run a variety of software applications.

One or more LANs 2104 may be coupled to WAN 2102. LAN 2104 may be a network that spans a relatively small area. Typically, LAN 2104 may be confined to a single building or group of buildings. Each node (i.e., individual computer system or device) on LAN 2104 may have its own Central Processing Unit (CPU) with which it may execute programs. Each node may also be able to access data and devices anywhere on LAN 2104. LAN 2104, thus, may allow many users to share devices (e.g., printers) and data stored on file servers. LAN 2104 may be characterized by a variety of types of topology (i.e., the geometric arrangement of devices on the network), of protocols (i.e., the rules and encoding specifications for sending data, and whether the network uses a peer-to-peer or client/server architecture), and of media (e.g., twisted-pair wire, coaxial cables, fiber optic cables, and/or radio waves).

Each LAN 2104 may include a plurality of interconnected computer systems (e.g., computers 201, 215*a*, 215*b*, 215*c*, etc.) and optionally one or more other devices. For example, LAN 2104 may include one or more workstations 2110*a*, one or more personal computers 2112*a*, one or more laptop or notebook computer systems 2114, one or more server computer systems 2116 (e.g., server 207), and one or more network printers 2118. As illustrated in FIG. 21, an example LAN 2104 may include one of each computer systems 2110*a*, 2112*a*, 2114, and 2116, and one printer 2118. LAN 2104 may be coupled to other computer systems and/or other devices and/or other LANs through WAN 2102.

One or more mainframe computer systems 2120 may be coupled to WAN 2102. As shown, mainframe 2120 may be coupled to a storage device or file server 2124 and mainframe terminals 2122*a*, 2122*b*, and 2122*c*. Mainframe terminals 2122*a*, 2122*b*, and 2122*c* may access data stored in the storage device or file server 2124 coupled to or included in mainframe computer system 2120.

WAN 2102 may also include computer systems connected to WAN 2102 individually and not through LAN 2104. For example, workstation 2110*b* and personal computer 2112*b* may be connected to WAN 2102. For example, WAN 2102 may include computer systems that may be geographically remote and connected to each other through the Internet.

Figure 22:
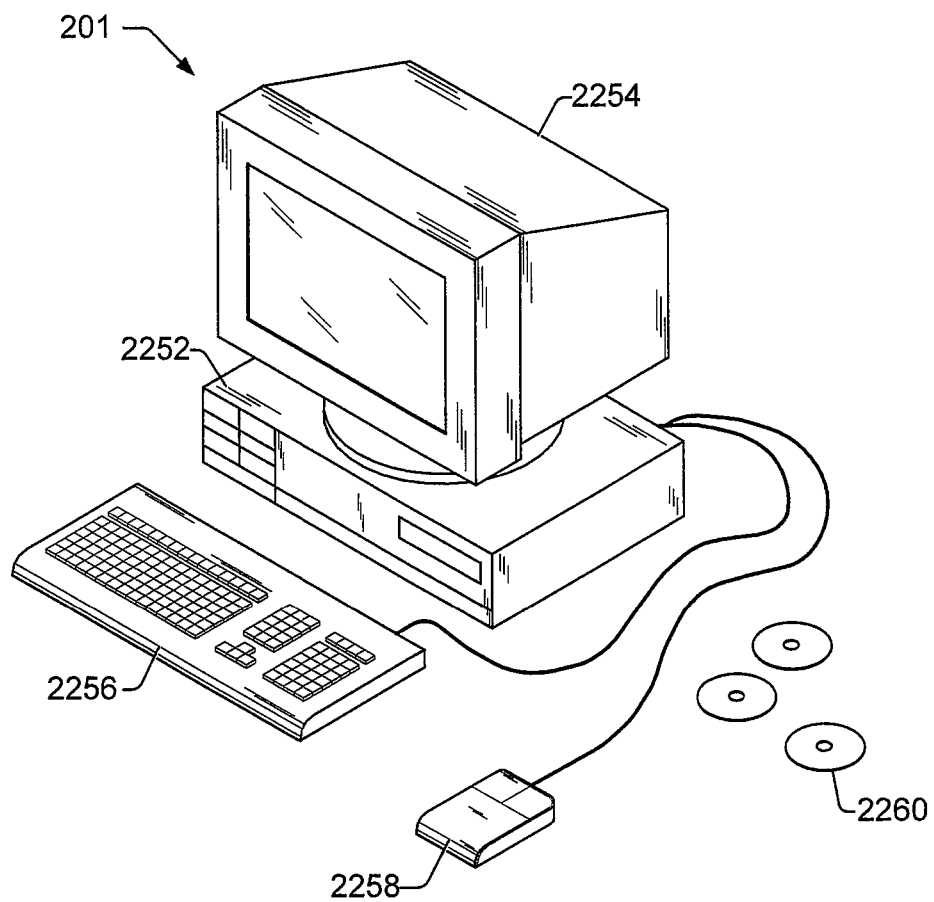
FIG. 22 illustrates an embodiment of computer system that may be suitable for implementing various embodiments of a system and method for substance delivery and monitoring.

FIG. 22 illustrates an embodiment of computer system 201 that may be suitable for implementing various embodiments of a system and method for test animal substance delivery and monitoring. Each computer system 201 typically includes components such as CPU 2252 with an associated memory medium such as Compact Disc Read Only Memories (CD-ROMs) 2260. The memory medium may store program instructions for computer programs. The program instructions may be executable by CPU 2252. Computer system 201 may further include a display device such as monitor 2254, an alphanumeric input device such as keyboard 2256, and a directional input device such as mouse 2258. Computer system 201 may be operable to execute the computer programs to implement computer-implemented systems and methods for test animal substance delivery and monitoring.

Computer system 201 may include a memory medium on which computer programs according to various embodiments may be stored. The term "memory medium" is intended to include an installation medium, e.g., floppy disks or Compact Disc Read Only Memories (CD-ROMs) 2260, a computer system memory such as Dynamic Random Access Memory (DRAM), Static Random Access Memory (SRAM), Extended Data Out Random Access Memory (EDO RAM), Double Data Rate Random Access Memory (DDR RAM), Rambus Random Access Memory (RAM), etc., or a non-volatile memory such as a magnetic media, e.g., a hard drive or optical storage. The memory medium may also include other types of memory or combinations thereof. In addition, the memory medium may be located in a first computer, which executes the programs or may be located in a second different computer, which connects to the first computer over a network. In the latter instance, the second computer may provide the program instructions to the first computer for execution. Computer system 201 may take various forms such as a personal computer system, mainframe computer system, workstation, network appliance, Internet appliance, PDA, television system or other device. In general, the term "computer system" may refer to any device having a processor that executes instructions from a memory medium.

The memory medium may store a software program or programs operable to implement a method for test animal substance delivery and monitoring. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes (MFC), browser-based applications (e.g., Java applets), traditional programs, or other technologies or methodologies, as desired. A CPU such as host CPU 2252 executing code and data from the memory medium may include a means for creating and executing the software program or programs according to the embodiments described herein.

Various embodiments may also include receiving or storing instructions and/or data implemented in accordance with the foregoing description upon a carrier medium. Suitable carrier media may include storage media or memory media such as magnetic or optical media, e.g., disk or CD-ROM, as well as signals such as electrical, electromagnetic, or digital signals, may be conveyed via a communication medium such as a network and/or a wireless link.

Embodiments of a subset or all (and portions or all) of the above may be implemented by program instructions stored in a memory medium or carrier medium and executed by a processor. A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, a computer system at a respective participant location may include a memory medium(s) on which one or more computer programs or software components according to one embodiment of the present invention may be stored. For example, the memory medium may store one or more programs that are executable to perform the methods described herein. The memory medium may also store operating system software, as well as other software for operation of the computer system.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system, comprising:
    a plurality of pumps operable to deliver a substance to a respective animal at a respective controlled delivery rate; and
    a computer system communicatively coupled to at least two of the plurality of pumps;
        wherein the computer system is operable to determine the respective controlled delivery rates of substance delivery based at least partially on a weight of the respective animal;
    wherein the computer system is operable to communicate the determined respective controlled delivery rates to the at least two respective pumps of the plurality of pumps;
    wherein the computer system is operable to receive a user identifier and a documentation indicator associated with a pump of the plurality of pumps; and
    wherein the computer system is operable to store the user identifier and the documentation indicator.

2. The system of claim 1, further comprising at least one weight scale communicatively coupled to the computer system, wherein the at least one weight scale is operable to weigh at least one respective animal associated with at least one pump of the plurality of pumps; and wherein weighing the at least one respective animal comprises weighing a cage containing the at least one respective animal.

3. The system of claim 1,
    wherein the at least two of the plurality of pumps are operable to communicate with at least one of: a personal digital assistant, a cell phone, or a smart card; and
    wherein the computer system is operable to communicate with at least one of: a personal digital assistant, a cell phone, or a smart card.

4. The system of claim 1, wherein the computer system is further operable to generate a list of future substance amounts for syringes for at least two of the plurality of pumps of the plurality of pumps.

5. The system of claim 1, wherein the computer system is further operable to receive a separate user identifier for each of at least two separate documentation indicators, and to store the separate user identifiers and separate documentation indicators.

6. The system of claim 1, wherein the computer system is further operable to authenticate an operator using the received user identifier.

7. The system of claim 1, wherein the user identifier is an electronic signature stamp.

8. The system of claim 1, wherein the user identifier is a personal identification number (PIN) typed into the pump by an operator.

9. The system of claim 1, wherein the user identifier is electronically scanned or electronically transmitted into the pump.

10. The system of claim 1, wherein the user identifier is a scanned user biometric comprising a scanned thumbprint or a scanned retina.

11. The system of claim 1, wherein the documentation indicator is operable to indicate an alarm and an action taken to clear the alarm.

12. The system of claim 1, wherein the documentation indicator is operable to indicate an observation of an operator.

13. The system of claim 1, wherein the documentation indicator is received from a personal digital assistant communicating with a pump of the plurality of pumps or the computer system.

14. The system of claim 1, further comprising:
wherein the computer system is operable to provide an interface to an operator for generating a menu; and
wherein the pump is operable to provide the menu to the operator, wherein a response to the menu from the operator is received as a documentation indicator.

15. The system of claim 1, wherein the computer system or a pump of the plurality of pumps comprises:
a processor; and
a memory coupled to the processor and configured to store program instructions executable by the processor to:
receive a beginning syringe weight, wherein the beginning syringe weight comprises a weight of a syringe with a substance for delivery to an animal;
receive an ending syringe weight, wherein the ending syringe weight is determined after delivering a portion of the substance in the syringe;
determine an actual volume output, wherein the actual volume output is at least partially determined using the beginning syringe weight and the ending syringe weight;
compare the actual volume output to an expected volume output, wherein the expected volume output is determined from a calculated controlled delivery rate delivered to a pump configured to pump the substance from the syringe; and
determine if the comparison of the actual volume output to the expected volume output is approximately within an acceptable validation deviation.

16. The system of claim 1,
wherein the computer system is operable to access respective calibration information for the at least two of the plurality of pumps; and
wherein the computer system is further operable to prevent operation of a pump of the at least two pumps that are outside of a calibration interval or will be outside of the calibration interval during a study period.

17. The system of claim 1,
wherein the computer system is operable to determine an amount of a substance to load into a syringe;
wherein a computer system communicatively coupled to a pump, of the plurality of pumps, coupled to the syringe calculates the amount based at least partially on a controlled delivery rate assigned to an animal to receive the substance from the syringe; and
wherein the pump is operable to fill the syringe with the determined substance amount, wherein the pump is operable to receive the determined substance amount from the computer system.

18. The system of claim 1,
wherein the computer system is operable to send and receive information to and from the plurality of pumps;
wherein at least one pump of the plurality of pumps is operable to provide input data, received from an operator at the at least one pump, to the computer system.

19. A system, comprising:
a plurality of pumps operable to deliver a substance to a respective animal at a respective controlled delivery rate; and
a computer system communicatively coupled to at least two of the plurality of pumps;
wherein the computer system is operable to determine the respective controlled delivery rates of substance delivery;
wherein the computer system is further operable to communicate the determined respective controlled delivery rates to the at least two respective pumps of the plurality of pumps;
wherein the computer system is further operable to assign or receive assignments of one or more respective animals to a group of a plurality of groups, wherein the respective animals associated with the same group receive controlled delivery rates determined using at least one common variable.

20. The system of claim 19, wherein the computer system is operable to assign or receive assignments of one or more of the plurality of pumps to a group of a plurality of groups and wherein the respective animals associated with the same group are associated with respective pumps of the same group.

21. The system of claim 19, wherein the plurality of groups includes at least one substance concentration group and at least one control group.

22. The system of claim 19, wherein one group of the plurality of groups includes a high substance concentration group and one group includes a low substance concentration group, and wherein the respective pumps of the respective animals in the high substance concentration group receive respective controlled delivery rates determined using a higher substance concentration to animal weight ratio than the respective pumps of the respective animals in the low substance concentration group.

23. A system, comprising:
a plurality of pumps operable to deliver a substance to a respective animal at a respective controlled delivery rate; and
a computer system communicatively coupled to at least two of the plurality of pumps;
wherein the computer system is operable to determine the respective controlled delivery rates of substance delivery based at least partially on a weight of the respective animal, and to communicate the determined respective controlled delivery rates to the at least two respective pumps of the plurality of pumps;
wherein the computer system or a pump of the plurality of pumps comprises:
a processor; and
a memory coupled to the processor and configured to store program instructions executable by the processor to:
receive a beginning syringe weight, wherein the beginning syringe weight comprises a weight of a syringe with a substance for delivery to an animal;
receive an ending syringe weight, wherein the ending syringe weight is determined after delivering a portion of the substance in the syringe;

determine an actual volume output, wherein the actual volume output is at least partially determined using the beginning syringe weight and the ending syringe weight;

compare the actual volume output to an expected volume output, wherein the expected volume output is determined from a calculated controlled delivery rate delivered to a pump configured to pump the substance from the syringe; and determine if the comparison of the actual volume output to the expected volume output is approximately within an acceptable validation deviation.

24. A system, comprising:

a plurality of pumps operable to deliver a substance to a respective animal at a respective controlled delivery rate; and a computer system communicatively coupled to at least two of the plurality of pumps;

wherein the computer system is operable to determine the respective controlled delivery rates of substance delivery based at least partially on a weight of the respective animal, and to communicate the determined respective controlled delivery rates to the at least two respective pumps of the plurality of pumps; and wherein the computer system is operable to access respective calibration information for the at least two of the plurality of pumps, and to prevent operation of a pump of the at least two pumps that are outside of a calibration interval or will be outside of the calibration interval during a study period.

* * * * *